United States Patent
Jaminet et al.

(10) Patent No.: US 10,155,812 B2
(45) Date of Patent: Dec. 18, 2018

(54) TM4SF1 BINDING PROTEINS AND METHODS OF USING SAME

(71) Applicant: Beth Israel Deaconess Medical Center, Inc., Boston, MA (US)

(72) Inventors: Shou-Ching S. Jaminet, Cambridge, MA (US); Harold F. Dvorak, Newton Center, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 0 days.

(21) Appl. No.: 15/092,486

(22) Filed: Apr. 6, 2016

(65) Prior Publication Data

US 2016/0229910 A1    Aug. 11, 2016

Related U.S. Application Data

(63) Continuation of application No. PCT/US2014/059761, filed on Oct. 8, 2014.

(60) Provisional application No. 61/889,340, filed on Oct. 10, 2013.

(51) Int. Cl.
| | |
|---|---|
| C07K 16/28 | (2006.01) |
| C07K 16/30 | (2006.01) |
| A61K 39/395 | (2006.01) |
| G01N 33/574 | (2006.01) |
| A61K 47/48 | (2006.01) |
| G01N 33/68 | (2006.01) |
| A61K 39/00 | (2006.01) |

(52) U.S. Cl.
CPC ........ *C07K 16/28* (2013.01); *A61K 47/48561* (2013.01); *C07K 16/30* (2013.01); *G01N 33/574* (2013.01); *G01N 33/6893* (2013.01); *A61K 2039/505* (2013.01); *C07K 2317/14* (2013.01); *C07K 2317/34* (2013.01); *C07K 2317/51* (2013.01); *C07K 2317/515* (2013.01); *C07K 2317/77* (2013.01); *C07K 2317/92* (2013.01); *G01N 2333/705* (2013.01); *G01N 2800/7014* (2013.01)

(58) Field of Classification Search
None
See application file for complete search history.

(56) References Cited

U.S. PATENT DOCUMENTS

| | | | | |
|---|---|---|---|---|
| 4,997,913 | A | * | 3/1991 | Hellstrom .......... A61K 47/6883 424/181.1 |
| 5,869,045 | A | * | 2/1999 | Hellstrom .......... A61K 47/6851 424/130.1 |
| 2003/0073144 | A1 | * | 4/2003 | Benson ................. C07K 14/47 435/7.23 |
| 2011/0177970 | A1 | | 7/2011 | Chauchereau et al. |
| 2012/0070450 | A1 | | 3/2012 | Ishikawa et al. |
| 2013/0017208 | A1 | | 1/2013 | Chen et al. |

FOREIGN PATENT DOCUMENTS

| | | |
|---|---|---|
| WO | WO-00/56755 A1 | 9/2000 |
| WO | WO-00/77197 A1 | 12/2000 |
| WO | WO-2010/119704 A1 | 10/2010 |
| WO | WO-2012/027723 A1 | 3/2012 |

OTHER PUBLICATIONS

Vaughan et al., Nature Biotechnology, 1996, 14: 309-314.*
Paul, Fundamental Immunology, 3rd Edition, 1993, pp. 292-295.*
Rudikoff et al., Proc. Natl. Acad. Sci. USA, 79(6):1979-1983.*
Bendig, Methods: A Companion to Methods in Enzymology, 1995; 8:83-93.*
Khantasup et al., Monoclonal Antibodies in Immunodiagnosis and Immunotherapy, 2015, 34(6): 404-417.*
Portolano et al., Journal of Immunology, 1993, 150(3): 880-887.*
Colman P. M., Research in Immunology, 145:33-36, 1994.*
Lin et al., Angiogenesis, 2014, 17(4):897-907.*
Marken et al., "Membrane topology of the L6 antigen and identification of the protein epitope recognized by the L6 monoclonal antibody," J Biol Chem. 269(10):7397-401 (1994).
International Preliminary Report on Patentability for International Patent Application No. PCT/US2014/059761, dated Apr. 12, 2016 (6 pages).
International Search Report and Written Opinion for International Patent Application No. PCT/US2014/059761, dated Jan. 20, 2015 (9 pages).
Extended European Search Report for European Patent Application No. 14851712.1, dated Apr. 19, 2017 (6 pages).
Sciuto et al., "Intracellular Distribution of TM4SF1 and Internalization of TM4SF1-antibody Complex in Vascular Endothelial Cells," available in PMC Sep. 25, 2016, published in final edited form as: Biochem Biophys Res Commun. 465(3):338-43 (2015) (14 pages).
Zukauskas et al., "TM4SF1: A tetraspanin-like protein necessary for nanopodia formation and endothelial cell migration," Available in PMC Mar. 11, 2012, published in final edited form as: Angiogenesis. 14(3):345-354 (2011) (16 pages).

(Continued)

*Primary Examiner* — Hong Sang
(74) *Attorney, Agent, or Firm* — Clark & Elbing LLP

(57) ABSTRACT

This present invention relates to compounds (e.g., TM4SF1 binding proteins, e.g., anti-TM4SF1 antibodies) that specifically bind to a polypeptide at an epitope including an amino acid sequence of SEQ ID NO: 1. In particular, the compounds of the invention are capable of being internalized into a TM4SF1-expressing cell (e.g., a tumor cell or an angiogenic vasculature endothelial cell) following binding to the epitope of including the amino acid sequence of SEQ ID NO: 1. The invention also provides methods of treating a subject having a disorder associated with pathological angiogenesis with the compounds of the invention.

16 Claims, 14 Drawing Sheets
(13 of 14 Drawing Sheet(s) Filed in Color)
Specification includes a Sequence Listing.

(56) References Cited

OTHER PUBLICATIONS

Shih et al., "The L6 Protein TM4SF1 is Critical for Endothelial Cell Function and Tumor Angiogenesis," Available in PMC Apr. 15, 2010, published in final edited form as: Cancer Res. 69(8):3272-3277 (2009) (12 pages).

Visintin et al., "Novel Anti-TM4SF1 Antibody-Drug Conjugates with Activity against Tumor Cells and Tumor Vasculature," Mol Cancer Ther. 14(8): 1868-76 (2015).

\* cited by examiner

| Protein Domains | | amino acid # |
|---|---|---|
| N | N-terminal | 9 |
| TM1 | membrane 1 | 21 |
| ECL1 | extracellular loop 1 | 15 |
| TM2 | membrane 2 | 25 |
| ICL | intracellular loop 1 | 18 |
| TM3 | membrane 3 | 28 |
| ECL2 | extracellular loop 2 | 48 |
| TM4 | membrane 4 | 28 |
| C | C-terminal | 10 |

Figures 2A-2B
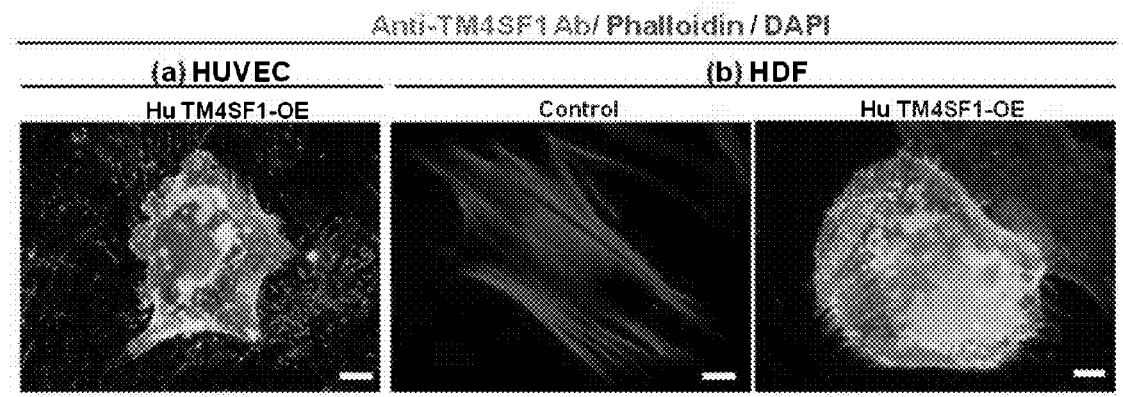
Figure 2A
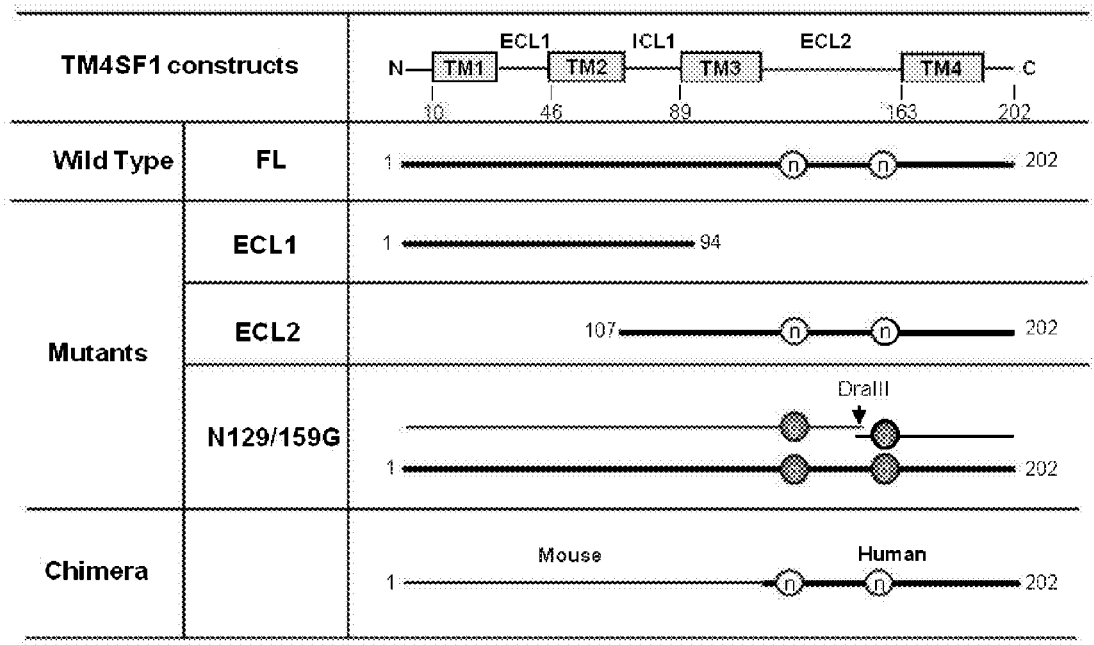
Figure 2B

Figures 2C-2D
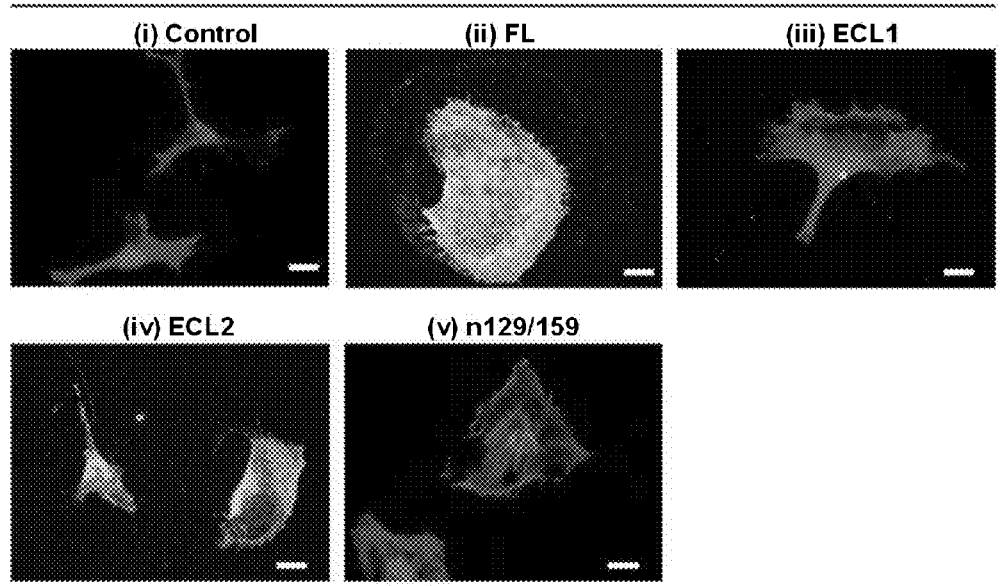
Figure 2C
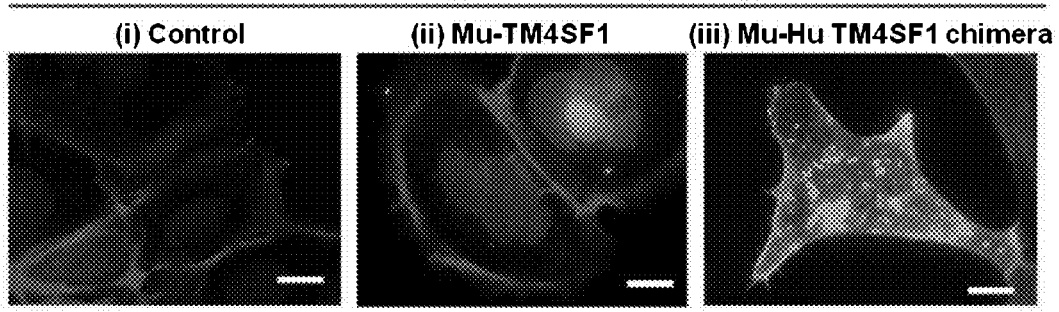
Figure 2D

```
                 L6 Hellstrom's Ab epitope                          8G4 epitope
                          ↓                                              ↓ 164
Human    117  EGPLCLDSLGQWNYTFASTEGQYLLDTSTWSECTEPKHIVEWNVSLFS              SEQ ID NO: 10
                   └──S────┘              └─S─┘

Monkey        EGPLCLDSFGQWNYTFASTEGQYLLDTSTWSQCTEPKHIVEWNVSLFS              SEQ ID NO: 11
                   └──S────┘              └─S─┘

Mouse         EGPKCSDAHGVWNYTFASTEGQYLLNSSMWSKCYEPKHIVEWHVTLFS              SEQ ID NO: 12
                   └──S────┘              └─S─┘
```

NXS – N-linked glycosylation site
Purple marks amino acid differences from human TM4SF1

Figure 2E

Figures 3A-3C
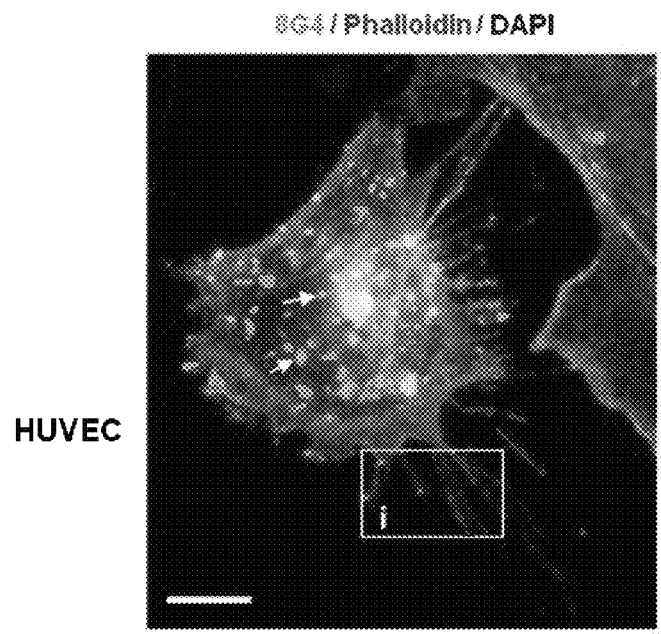
HUVEC
Figure 3A
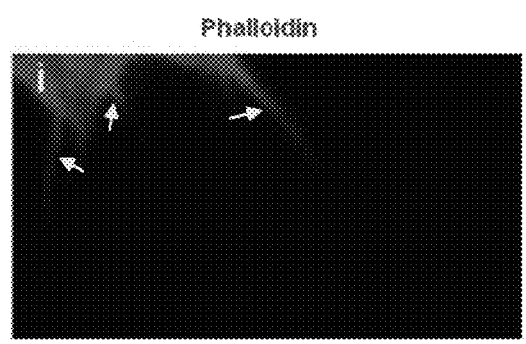
Figure 3B
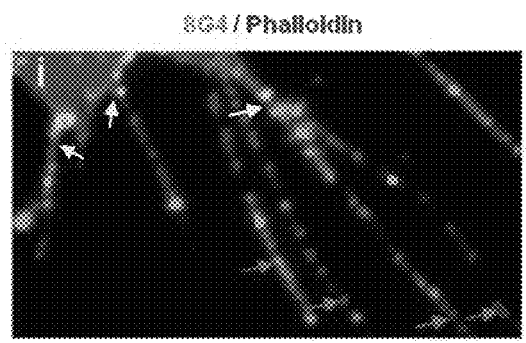
Figure 3C

Figures 3D-3F
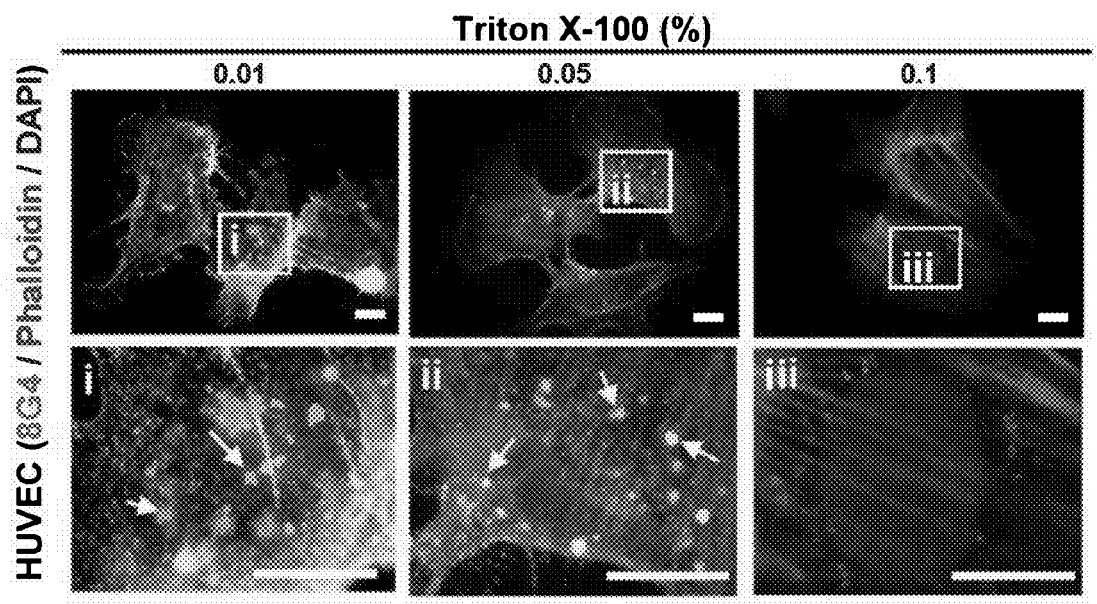
Figure 3D
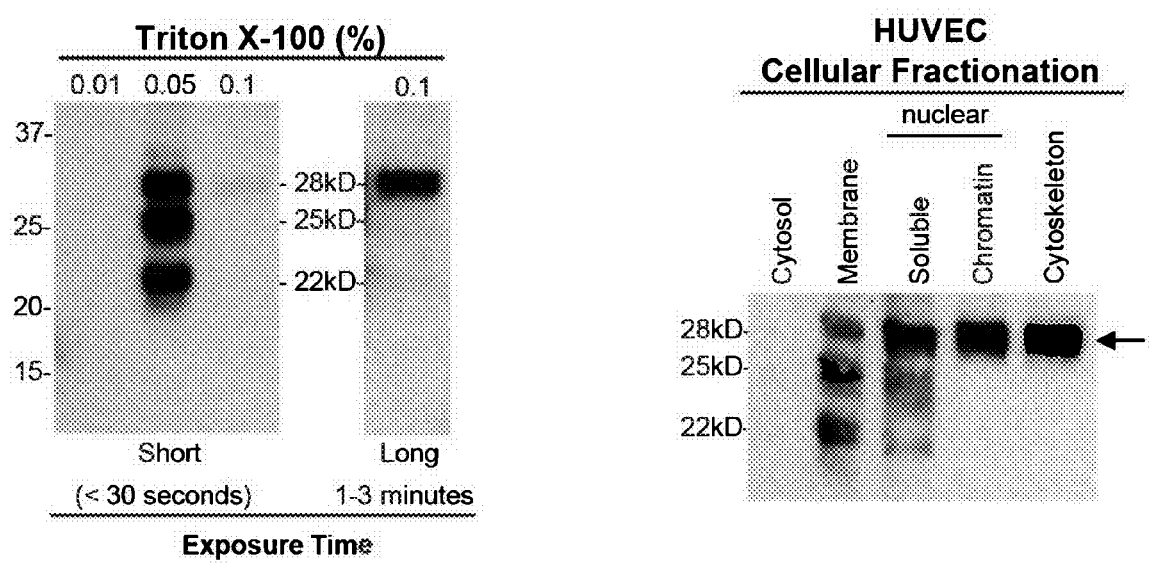
Figure 3E
Figure 3F

Figures 4A-4B
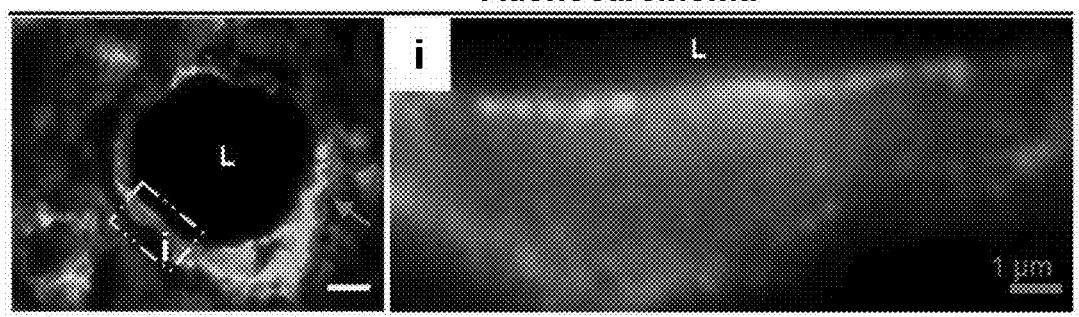
Figure 4A
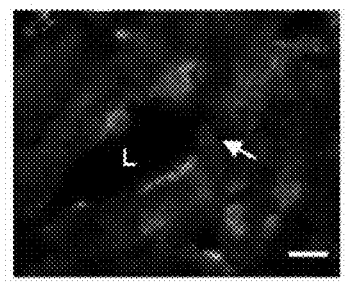
Figure 4B

Figures 4C-4F
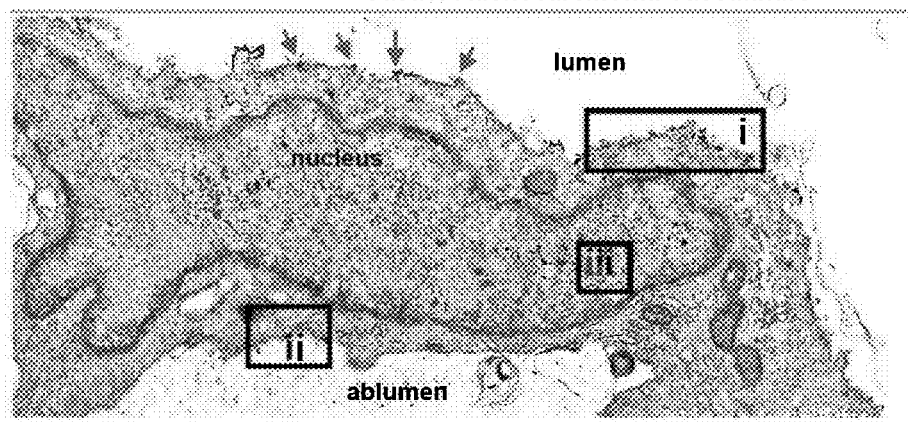
Figure 4C
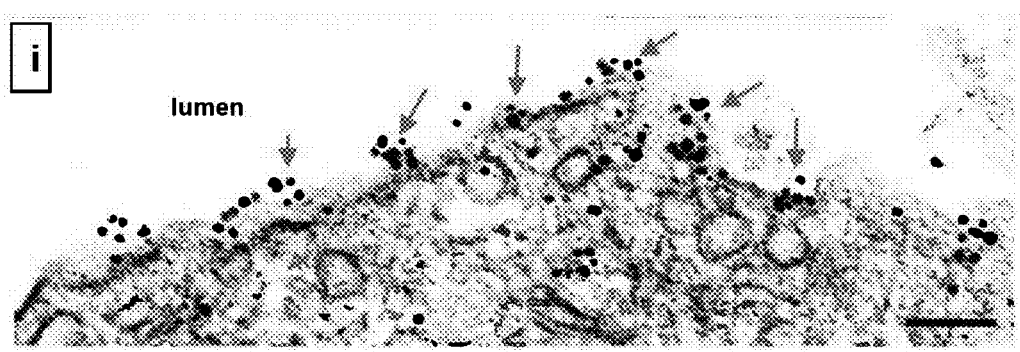
Figure 4D
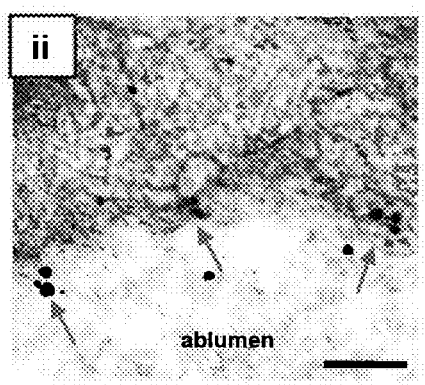
Figure 4E
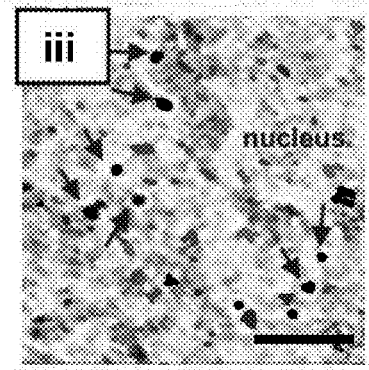
Figure 4F Figures 4G-4H
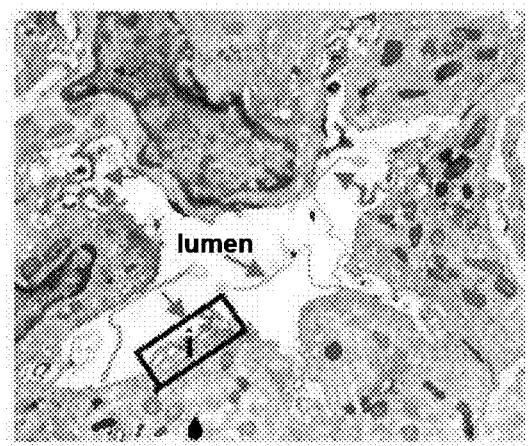
Figure 4G
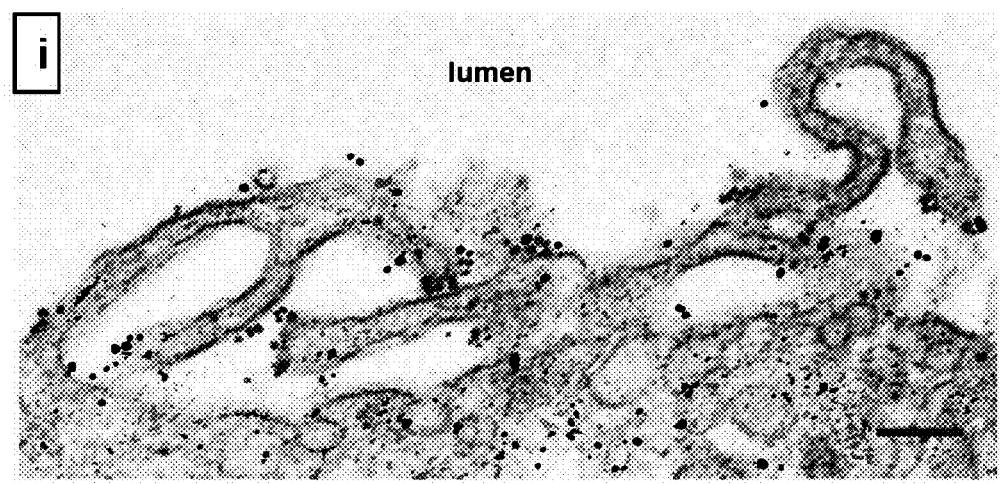
Figure 4H Figures 4I-4J
Adjacent normal vasculature
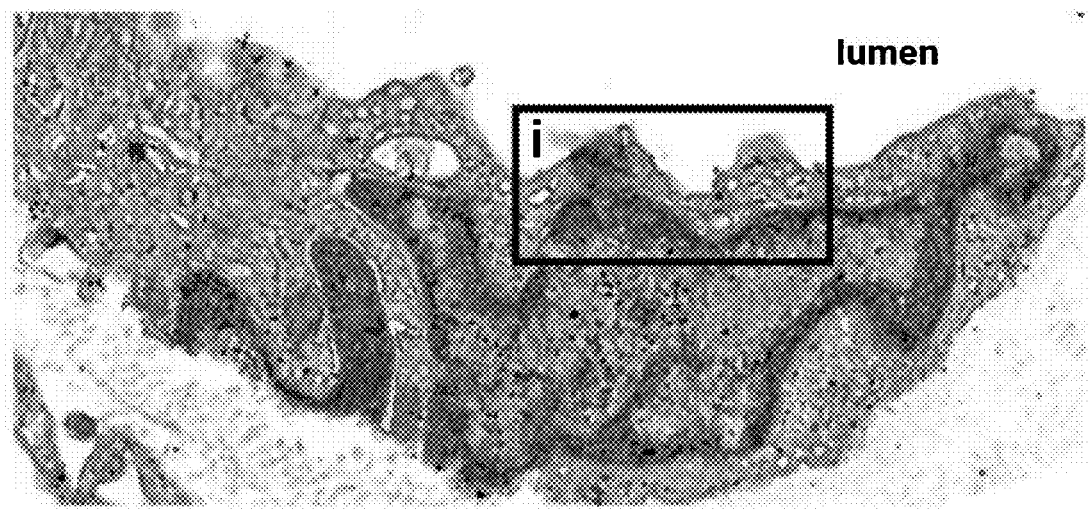
Figure 4I
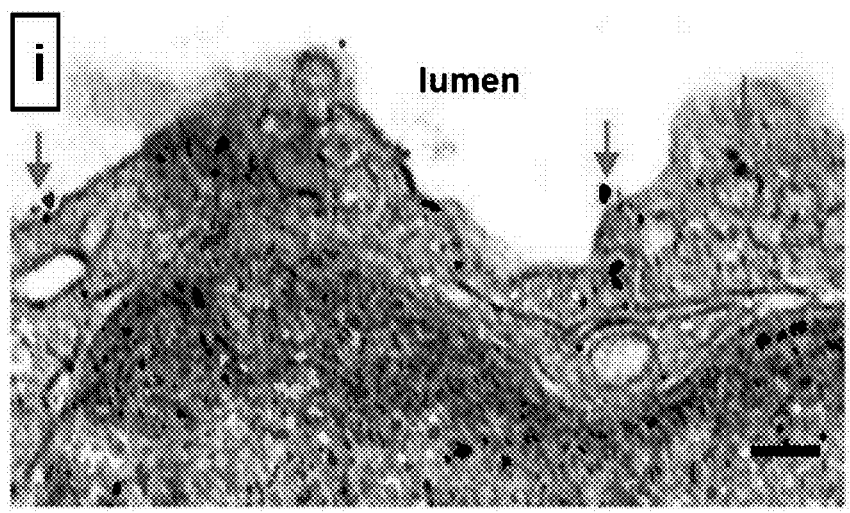
Figure 4J

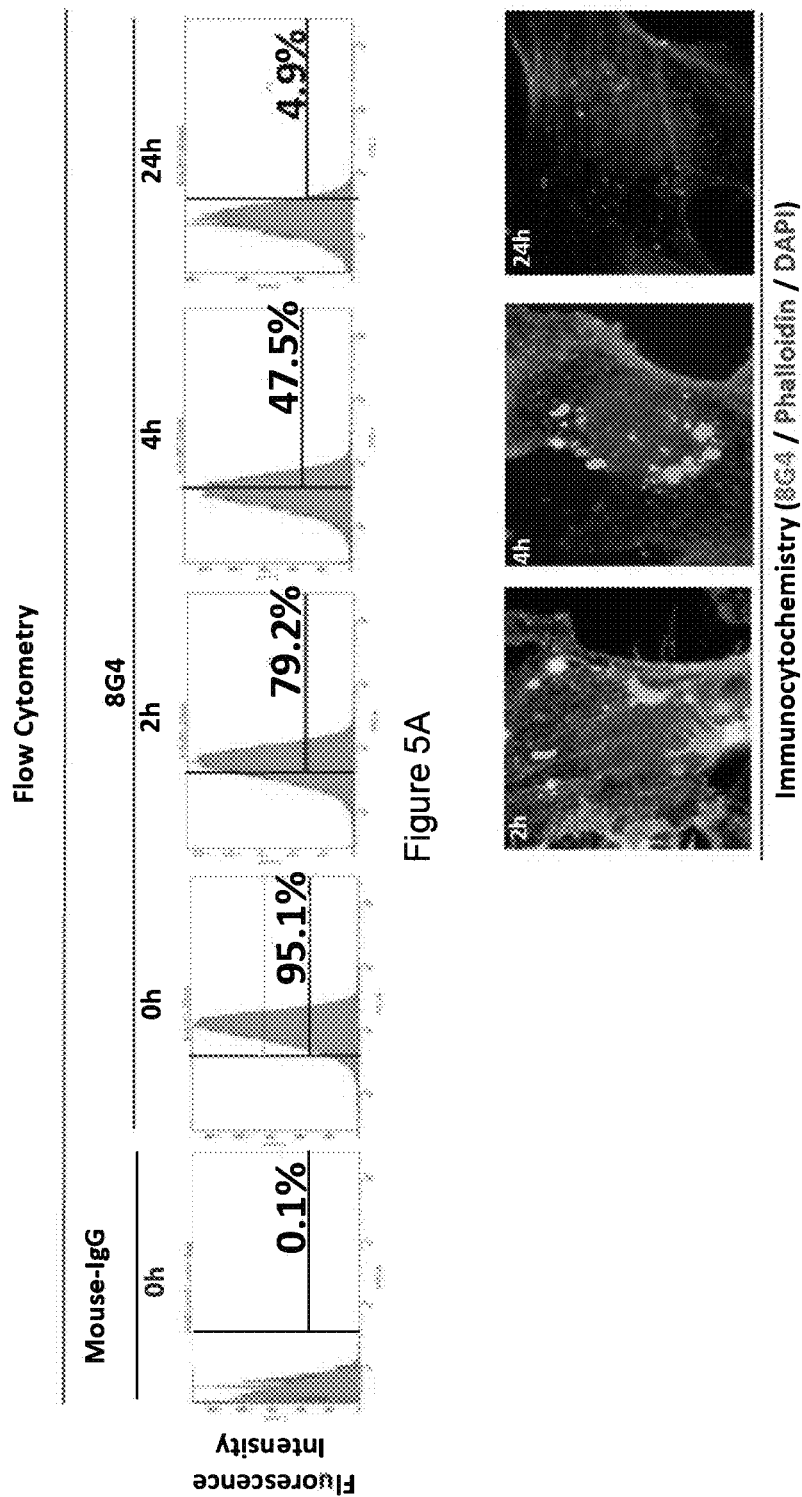

Figures 5C-5F
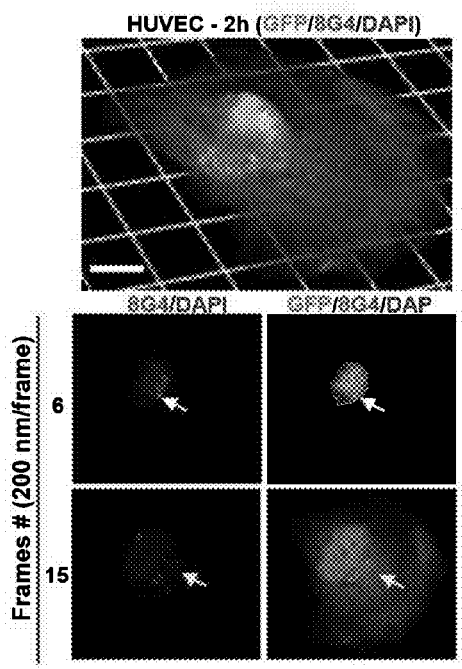
Figure 5C
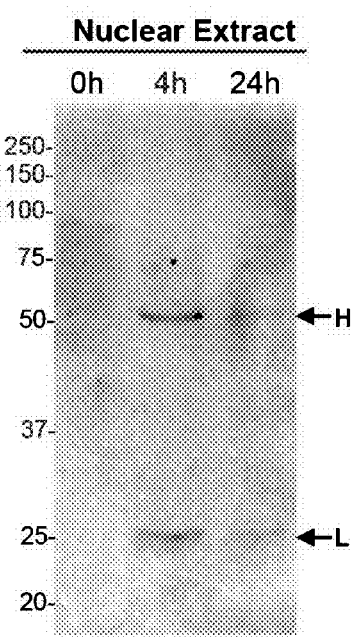
Figure 5D
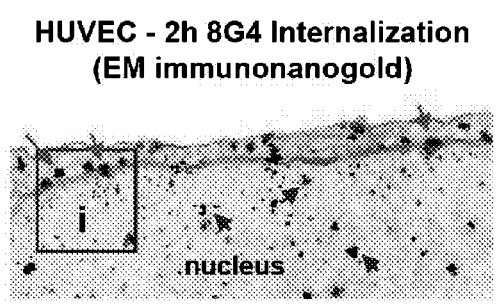
Figure 5E
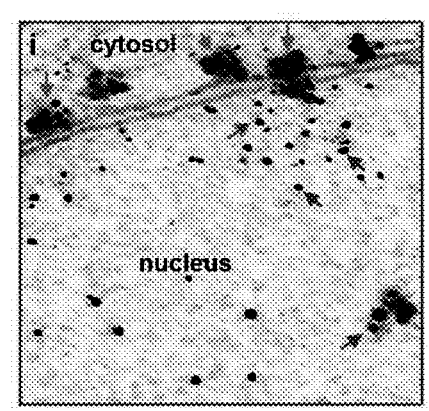
Figure 5F Figures 6A-6C
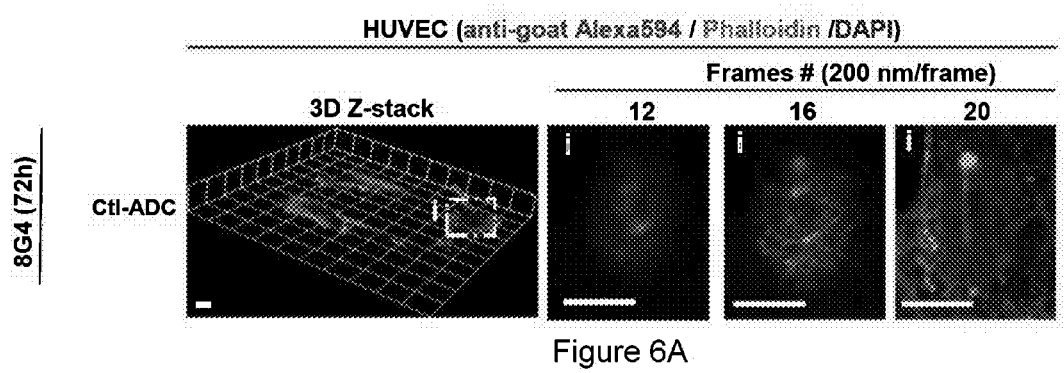
Figure 6A
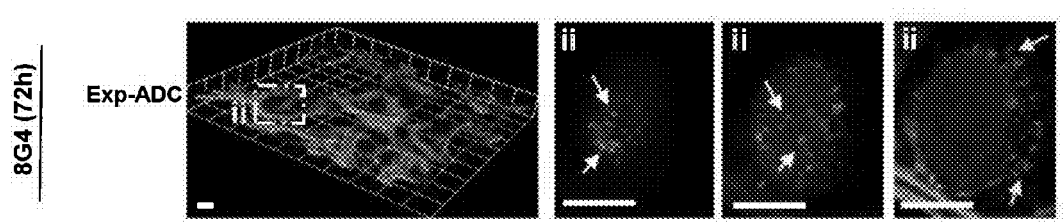
Figure 6B
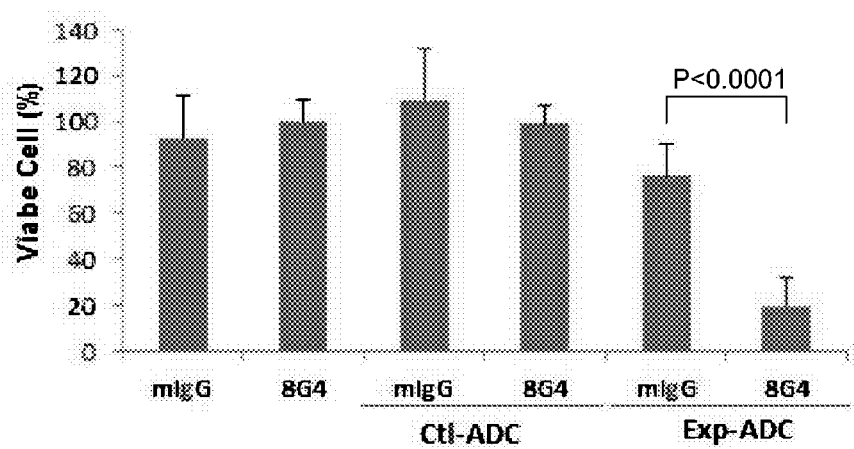
Figure 6C

SEQUENCE LISTING

<160> NUMBER OF SEQ ID NOS: 9

<210> SEQ ID NO 1
<211> LENGTH: 33
<212> TYPE: PRT
<213> ORGANISM: Artificial Sequence
<220> FEATURE:
<223> OTHER INFORMATION: Synthetic Construct

<400> SEQUENCE: 1

Asn Tyr Thr Phe Ala Ser Thr Glu Gly Gln Tyr Leu Leu Asp Thr Ser
1               5                   10                  15

Thr Trp Ser Glu Cys Thr Glu Pro Lys His Ile Val Glu Trp Asn Val
            20                  25                  30

Ser

<210> SEQ ID NO 2
<211> LENGTH: 10
<212> TYPE: PRT
<213> ORGANISM: Artificial Sequence
<220> FEATURE:
<223> OTHER INFORMATION: Synthetic Construct

<400> SEQUENCE: 2

Gly Phe Thr Phe Ser Ser Phe Ala Met Ser
1               5                   10

<210> SEQ ID NO 3
<211> LENGTH: 17
<212> TYPE: PRT
<213> ORGANISM: Artificial Sequence
<220> FEATURE:
<223> OTHER INFORMATION: Synthetic Construct

<400> SEQUENCE: 3

Thr Ile Ser Ser Gly Ser Ile Tyr Ile Tyr Tyr Thr Asp Gly Val Lys
1               5                   10                  15

Gly

<210> SEQ ID NO 4
<211> LENGTH: 14
<212> TYPE: PRT
<213> ORGANISM: Artificial Sequence
<220> FEATURE:
<223> OTHER INFORMATION: Synthetic Construct

<400> SEQUENCE: 4

Arg Gly Ile Tyr Tyr Gly Tyr Asp Gly Tyr Ala Met Asp Tyr
1               5                   10

<210> SEQ ID NO 5
<211> LENGTH: 16
<212> TYPE: PRT
<213> ORGANISM: Artificial Sequence
<220> FEATURE:
<223> OTHER INFORMATION: Synthetic Construct

<400> SEQUENCE: 5

Arg Ser Ser Gln Ser Leu Val His Ser Asn Gly Asn Thr Tyr Leu His
1               5                   10                  15

<210> SEQ ID NO 6
<211> LENGTH: 7
<212> TYPE: PRT
<213> ORGANISM: Artificial Sequence
<220> FEATURE:
<223> OTHER INFORMATION: Synthetic Construct

<400> SEQUENCE: 6

Lys Val Ser Asn Arg Phe Ser
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic Construct

<400> SEQUENCE: 7

Ser Gln Ser Thr His Val Tyr Thr
1               5

<210> SEQ ID NO 8
<211> LENGTH: 123
<212> TYPE: PRT
<213> ORGANISM: Artificial Sequence
<220> FEATURE:
<223> OTHER INFORMATION: Synthetic Construct

<400> SEQUENCE: 8

Glu Val Ile Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Phe
                20                  25                  30

Ala Met Ser Trp Val Arg Gln Thr Pro Glu Lys Arg Leu Glu Trp Val
            35                  40                  45

Ala Thr Ile Ser Ser Gly Ser Ile Tyr Ile Tyr Tyr Thr Asp Gly Val
        50                  55                  60

Lys Gly Arg Phe Thr Ile Ser Arg Asp Asn Ala Lys Asn Thr Val His
65                  70                  75                  80

Leu Gln Met Ser Ser Leu Arg Ser Glu Asp Thr Ala Met Tyr Tyr Cys
                85                  90                  95

Ala Arg Arg Gly Ile Tyr Tyr Gly Tyr Asp Gly Tyr Ala Met Asp Tyr
            100                 105                 110

Trp Gly Gln Gly Thr Ser Val Thr Val Ser Ser
        115                 120

<210> SEQ ID NO 9
<211> LENGTH: 112
<212> TYPE: PRT
<213> ORGANISM: Artificial Sequence
<220> FEATURE:
<223> OTHER INFORMATION: Synthetic Construct

<400> SEQUENCE: 9

Ala Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
                20                  25                  30

Asn Gly Asn Thr Tyr Leu His Trp Tyr Met Gln Lys Pro Gly Gln Ser
            35                  40                  45

Pro Lys Val Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

```
Ser Arg Val Glu Ala Asp Asp Leu Gly Ile Tyr Phe Cys Ser Gln Ser
                85                  90                  95

Thr His Ile Pro Leu Ala Phe Gly Ala Gly Thr Lys Leu Glu Leu Lys
            100                 105                 110
```

TM4SF1 BINDING PROTEINS AND METHODS OF USING SAME

STATEMENT AS TO FEDERALLY FUNDED RESEARCH

This invention was made with government support under Grant No. CA092644, awarded by the National Institutes of Health (NIH). The government has certain rights in the invention.

BACKGROUND OF THE INVENTION

Angiogenesis is an important cellular event in which vascular endothelial cells (ECs) proliferate, prune, and reorganize to form new vessels from preexisting vascular networks. There is compelling evidence that the development of a vascular supply is essential for normal and pathological proliferative processes. Delivery of oxygen and nutrients, as well as the removal of catabolic products, represent rate-limiting steps in the majority of growth processes occurring in multicellular organisms. Thus, it has been generally assumed that the vascular compartment is necessary not only for organ development and differentiation during embryogenesis, but also for wound healing and reproductive functions in the adult.

Angiogenesis is also implicated in the pathogenesis of a variety of disorders, including but not limited to, cancers, obesity, proliferative retinopathies, age-related macular degeneration, tumors, rosacea, atheroscleroses, rheumatoid arthritis (RA), cellular immunity, and psoriasis. Angiogenesis is a cascade of processes consisting of degradation of the extracellular matrix of a local venue after the release of proteases, proliferation of capillary ECs, and migration of capillary tubes toward the angiogenic stimulus. In view of the remarkable physiological and pathological importance of angiogenesis, much work has been dedicated to the elucidation of the factors capable of regulating this process.

Transmembrane-4 L six family member-1 (TM4SF1) was discovered in 1986 as "L6 antigen" or "tumor cell antigen" (Hellstrom et al. Cancer Res. 46: 3917-3923, 1986) because it was abundantly expressed on many cancer cells. Unexpectedly, it was also found to be weakly expressed on the vascular ECs of blood vessels supplying normal tissues (DeNardo et al. Int J Rad Appl Instrum B. 18: 621-631, 1991; Wright et al. Protein Sci. 9: 1594-1600, 2000; Richman et al. Cancer Res. 5916s-5920s, 1995; O'Donnell et al. Prostate. 37: 91-97, 1998). TM4SF1 is highly expressed by the EC lining the blood vessels supplying several human cancers (Shih et al. Cancer Res. 69: 3272-3277, 2009; Zukauskas et al. Angiogenesis. 14: 345-354, 2011), by the ECs of developing retinal vasculature (English et al. J Biomed Inform. 42: 287-295, 2009), and by the ECs of angiogenic blood vessels induced in mice with an adenovirus expressing VEGF-A (Shih et al. Cancer Res. 69: 3272-3277, 2009), though not by many other cell types (Shih et al. Cancer Res. 69: 3272-3277, 2009; Zukauskas et al. Angiogenesis. 14: 345-354, 2011).

Despite findings suggesting that TM4SF1 has potential as a vascular target for treating disorders associated with pathological angiogenesis, such as cancers, there remains an unmet need for compounds that target TM4SF1 (e.g., TM4SF1-specific binding polypeptides, e.g., anti-TM4SF1 antibodies, e.g., anti-human TM4SF1 antibodies) and are useful and scalable for commercial and therapeutic purposes.

SUMMARY OF THE INVENTION

The invention is in part based on the identification of compounds (e.g., antibodies) that specifically bind TM4SF1 (e.g., at a particular epitope on the ECL2 domain of TM4SF1) with properties that indicate that they are particularly advantageous for therapy (e.g., the treatment of disorders associated with pathological angiogenesis, e.g., cancers).

In a first aspect, the invention features a compound including a binding domain that specifically binds to a polypeptide at an epitope comprising an amino acid sequence NYTFASTEGQYLLDTSTWSECTEPKH-IVEWNVS (SEQ ID NO: 1). In some embodiments, the polypeptide is transmembrane-4 L six family member-1 (TM4SF1). In some embodiments, the TM4SF1 is a human TM4SF1. In some embodiments, the human TM4SF1 is a glycosylated (e.g., N-glycosylated) human TM4SF1. In some embodiments, the glycosylated human TM4SF1 is glycosylated at residue N129 or residue N159. In some embodiments, the glycosylated human TM4SF1 is glycosylated at residue N129 and residue N159. In some embodiments, the compound is capable of specifically binding the glycosylated human TM4SF1 with a Kd value that is 10 nM or less (e.g., 10 nM, 5 nM, 2 nM, 1 nM, 500 pM, 100 pM, 50 pM, 1 pM, or 500 fM or less). In some embodiments, the binding domain of the compound includes at least one amino acid sequence (e.g., 1, 2, 3, 4, 5, or 6 amino acid sequences) selected from the group consisting of GFTFSSFAMS (SEQ ID NO: 2), TISSGSIYIYYTDGVKG (SEQ ID NO: 3), RGIYYGYDGYAMDY (SEQ ID NO: 4), RSSQSLVH-SNGNTYLH (SEQ ID NO: 5), KVSNRFS (SEQ ID NO: 6), and SQSTHIPLA (SEQ ID NO: 7). In some embodiments, the binding domain includes at least one, at least two, or all three amino acid sequences selected from: GFTFSSFAMS (SEQ ID NO: 2), TISSGSIYIYYTDGVKG (SEQ ID NO: 3), and RGIYYGYDGYAMDY (SEQ ID NO: 4). In some embodiments, the compound includes a binding domain including at least one, at least two, or all three amino acid sequences selected from: RSSQSLVHSNGNTYLH (SEQ ID NO: 5), KVSNRFS (SEQ ID NO: 6), and SQSTHIPLA (SEQ ID NO: 7). In some embodiments, the compound includes a binding domain including the following six amino acid sequences: GFTFSSFAMS (SEQ ID NO: 2), TISSGSI-YIYYTDGVKG (SEQ ID NO: 3), RGIYYGYDGYAMDY (SEQ ID NO: 4), RSSQSLVHSNGNTYLH (SEQ ID NO: 5), KVSNRFS (SEQ ID NO: 6), and SQSTHIPLA (SEQ ID NO: 7).

In some embodiments, the compound is an antibody. In some embodiments, the antibody is produced by a hybridoma mouse cell line 8G4-5-13-13F (PTA-120523). In some embodiments, the heavy chain of the antibody includes an amino acid sequence having at least 60%, 65%, 70%, 75%, or 80% sequence identity (e.g., 81%, 82%, 83%, 84%, 85%, 86%, 87%, 88%, 89%, 90%, 91%, 92%, 93%, 94%, 95%, 96%, 97%, 98%, 99%, or 100% identity) to EVILVESGGGLVKPGGSLKLSCAASGFTFSSFAM-SWVRQTPEKRLEWVATISSGSIYIYYTDGVKGR-FTISRD NAKNTVHLQMSSLRSEDTAMYYCARRGI-YYGYDGYAMDYWGQGTSVTVSS (SEQ ID NO: 8). In some embodiments, the light chain of the antibody includes an amino acid sequence having at least 60%, 65%, 70%, 75%, or 80% sequence identity (e.g., 81%, 82%, 83%, 84%, 85%, 86%, 87%, 88%, 89%, 90%, 91%, 92%, 93%, 94%, 95%, 96%, 97%, 98%, 99%, or 100% identity) to AVVMTQTPLSLPVSLGDQASISCRSSQSLVHSNGN-TYLHWYMQKPGQSPKVLIYKVSNRFSGVPDRFSGSG SGTDFTLKISRVEADDLGIYFCSQSTHIPLAFGAGT-KLELK (SEQ ID NO: 9). In some embodiments, the heavy chain of the antibody includes an amino acid sequence having at least 60%, 65%, 70%, 75%, or 80% sequence identity (e.g., 81%, 82%, 83%, 84%, 85%, 86%, 87%, 88%, 89%, 90%, 91%, 92%, 93%, 94%, 95%, 96%, 97%, 98%, 99%, or 100% identity) to EVILVESGGGLVKPGGSLKLS-CAASGFTFSSFAMSWVRQTPEKRLEWVATISSGSIYI-YYTDGVKGRFTISRD NAKNTVHLQMSSLRSED-TAMYYCARRGIYYGYDGYAMDYWGQGTSVTVSS (SEQ ID NO: 8), and the light chain of the antibody includes an amino acid sequence having at least 60%, 65%, 70%, 75%, or 80% sequence identity (e.g., 81%, 82%, 83%, 84%, 85%, 86%, 87%, 88%, 89%, 90%, 91%, 92%, 93%, 94%, 95%, 96%, 97%, 98%, 99%, or 100% identity) to AVVMTQTPLSLPVSLGDQASISCRSSQSLVHSNGN-TYLHWYMQKPGQSPKVLIYKVSNRFSGVPDRFSGSG SGTDFTLKISRVEADDLGIYFCSQSTHIPLAFGAGT-KLELK (SEQ ID NO: 9). In some embodiments, the antibody is monoclonal, humanized, chimeric, or synthetic. In some embodiments, the antibody is an antibody fragment. In some embodiments, the compound (e.g., antibody) is naked, unconjugated, and/or unmodified.

In some embodiments, the compound further includes an agent. In some embodiments, the agent is a therapeutic agent or a diagnostic agent. In some embodiments, the therapeutic agent is a biologically active moiety. In some embodiments, the biologically active moiety is selected from the group consisting of a cytotoxic agent, a chemotherapeutic agent, a protein, a peptide, an antibody, a growth inhibitory agent, and an anti-hormonal agent. In some embodiments, the cytotoxic agent is selected from the group consisting of a ribosome inactivating protein, a histone deacetylase (HDAC) inhibitor, a tubulin inhibitor, an alkylating agent, an antibiotic, an antineoplastic agent, an antiproliferative agent, an antimetabolite, a topoisomerase I or II inhibitor, a hormonal agonist or antagonist, an immunomodulator, a DNA minor groove binder, and a radioactive agent. In certain embodiments, the ribosome inactivating protein is saporin. In some embodiments, the diagnostic agent is a label. In some embodiments, the label is a fluorescent label, a chromogenic label, or a radiolabel. In some embodiments, the agent is directly conjugated to the compound. In other embodiments, the agent is indirectly conjugated to the compound, optionally by a linker.

In a second aspect, the invention features a pharmaceutical composition including a compound of the first aspect. In some embodiments, the pharmaceutical composition further includes a pharmaceutically acceptable carrier, excipient, and/or diluent. In some embodiments, the pharmaceutical composition is formulated for treating a disorder associated with pathological angiogenesis in a subject.

In a third aspect, the invention features a polynucleotide encoding one or more polypeptides of the first aspect. One or more polynucleotides of the third aspect may optionally be included in a vector (e.g., a recombinant expression vector).

In a fourth aspect, the invention features a host cell including one or more polynucleotides and/or vectors of the third aspect. In some embodiments, the host cell is a mammalian cell (e.g., HUVEC, CHO, HeLa, 3T3, BHK, COS, 293, and Jurkat cells). In other embodiments, the host cell is a prokaryotic cell (e.g., an *E. coli* cell).

In a fifth aspect, the invention features a method of producing a compound of the first aspect that includes culturing a host cell of the fourth aspect in a culture medium. In some embodiments, the method further includes recovering the polypeptide from the host cell or the culture medium. In some embodiments, the method is performed in vitro or ex vivo.

In a sixth aspect, the invention features a method of treating a subject having a disorder associated with pathological angiogenesis (e.g., cancer) including administering a therapeutically effective amount of the composition of the second aspect to the subject, thereby treating the subject. In some embodiments, the composition is administered to the subject in a dosage of about 0.01 mg/kg/4 days to about 10 mg/kg/4 days. In some embodiments, the composition is administered to the subject in a dosage of about 0.1 mg/kg/4 days to about 10 mg/kg/4 days. In some embodiments, the composition is administered to the subject in a dosage of about 3 mg/kg/wk to about 10 mg/kg/wk.

In any embodiment of the sixth aspect, the disorder associated with pathological angiogenesis may be cancer. In some embodiments, the cancer is selected from the group consisting of breast cancer, ovarian cancer, renal cancer, colorectal cancer, liver cancer, gastric cancer, stomach cancer, skin cancer, esophageal cancer, kidney cancer, brain cancer, thyroid cancer, prostate cancer, pancreatic cancer, and lung cancer, testicular cancer, small bowel cancer, salivary gland cancer, and adrenal cancer. In other embodiments, the disorder associated with pathological angiogenesis is obesity, macular degeneration, diabetic retinopathy, psoriasis, rheumatoid arthritis, cellular immunity, atherosclerosis, or rosacea.

In any embodiment of the sixth aspect, the compound may be capable of being internalized into a TM4SF1-expressing cell following binding to the epitope comprising an amino acid sequence NYTFASTEGQYLLDTSTWSECTEPKH-IVEWNVS (SEQ ID NO: 1). In some embodiments, the compound is internalized into the cytoplasm of the TM4SF1-expressing cell. In some embodiments, the compound is internalized into the nucleus of the TM4SF1-expressing cell. In some embodiments, the TM4SF1-expressing cell is a tumor vascular EC or a tumor cell.

In some embodiments, the composition of the second aspect is administered intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularly, mucosally, intrapericardially, intraumbilically, intraocularly, orally, topically, locally, by inhalation, by injection, by infusion, by continuous infusion, by localized perfusion bathing target cells directly, by catheter, by lavage, in cremes, or in lipid compositions. In some embodiments, the composition may be administered by localized drug delivery. In some embodiments, the localized drug delivery system results in the slow release of the composition. In some embodiments, the subject is administered at least one dose (e.g., 1, 2, 3, 4, 5, 6, 7, 8, 9, 10, or more doses) of the composition or is administered at least one dose (e.g., 1, 2, 3, 4, 5, 6, 7, 8, 9, 10, or more doses) daily, weekly, monthly, or yearly. The administration period may be defined (e.g., 1-4 weeks, 1-12 months, 1-20 years) or may be for the life of the subject. In other embodiments, the subject is administered in at least two doses (e.g., 2, 3, 4, 5, 6, 7, 8, 9, 10, or more doses) of the composition. In yet other embodiments, the composition is administered to the subject between one and seven times a week. When treating disorders associated with pathological angiogenesis (e.g., cancer), the composition(s) of the second aspect of the invention may be administered to the subject either before the occurrence of symptoms of disorder associated with pathological angiogenesis (e.g., cancer) or a definitive diagnosis, or after diagnosis or symptoms become evident. The composition(s) may be administered, for example, immediately after diagnosis or the clinical recognition of symptoms or 2, 4, 6, 10, 15, or 24 hours, 2, 3, 5, or 7 days, 2, 4, 6 or 8 weeks, or even 3, 4, or 6 months after diagnosis or detection of symptoms.

In a seventh aspect, the invention features a method detecting a polypeptide including an amino acid sequence NYTFASTEGQYLLDTSTWSECTEPKHIVEWNVS (SEQ ID NO: 1) in a biological sample, the method including the steps of: (a) providing the biological sample and a control sample; (b) contacting the biological sample and the control sample with the compound of the first aspect or a pharmaceutical composition of the second aspect; and (c) determining an amount of a complex of the compound and the polypeptide present in the biological sample and the control sample. In some embodiments, the biological sample is obtained from a subject suspected of having a disorder associated with pathological angiogenesis (e.g., cancer).

In a final aspect, the invention features a kit including: (a) a pharmaceutical composition of the second aspect of the invention; and (b) instructions for administering the pharmaceutical composition to a subject to treat a disorder associated with pathological angiogenesis (e.g., cancer).

In preferred embodiments of all aspects of the invention, the subject is a mammal, preferably a human.

BRIEF DESCRIPTION OF THE DRAWINGS

The application file contains at least one drawing executed in color. Copies of this patent or patent application with color drawings will be provided by the Office upon request and payment of the necessary fee.

FIG. 2A is a series of images depicting the initial screening, performed with immunocytochemistry using the 8G4 antibody, which identified 15 clones that were positive against HUVEC ((a) left panel) and HDF (human dermal fibroblasts) ((b), right panel, with center panel as HDF control) that had been transduced to overexpress human TM4SF1 (TM4SF1-OE), but did not stain native HDF that expressed TM4SF1 at extremely low levels (~5 mRNA copies/cell).

FIG. 2B is a diagram of the TM4SF1 wild-type, mutant, and mouse-human TM4SF1 chimeric constructs used in epitope mapping experiments. Epitope mapping was performed by immunocytochemistry on various TM4SF1 constructs that were transduced into HEMn (Human Epidermal Melanocytes, neonatal) cells that do not express TM4SF1 at detectable levels. Domain information was obtained from the Human Protein Reference Database. FL (full-length) TM4SF1 protein; ECL1, mutant expressing extracellular loop 1; ECL2, mutant expressing extracellular loop 2; N129/159G, two asparagines for N-glycosylation at amino acid positions 129 and 159 mutated to glycine. In the case of N129/159G, two separate PCR fragments were prepared, cut with DraIII restriction enzyme, and then ligated with T4 DNA ligase. The murine-human chimera (Mu-Hu TM4SF1) contains the human TM4SF1 sequence beginning at amino acid 117 and was chemically synthesized by Integrated DNA Technology (Coraville, Iowa). Each construct was expressed at ~500 mRNA copies/cell.

FIG. 2C is a series of images showing that the 8G4 antibody specifically binds to an epitope on ECL2 in a glycosylation-dependent manner. HEMn were transduced with (i) empty vector control, (ii) FL-TM4SF1, (iii) ECL1, (iv) ECL2, or (v) N129/159G for staining with 8G4 and phalloidin. Staining was lost when ECL2 was absent (iii) or when both n-glycosylated regions were mutated (v).

FIG. 2D is a series of images of 8G4 immunostaining of HEK293 cells that were transfected to express (i) empty vector control, (ii) murine TM4SF1 (Mu-TM4SF1), or (iii) Mu-Hu TM4SF1 chimera. 8G4 recognized the Mu-Hu TM4SF1 chimera but not native murine TM4SF1.

FIG. 2E is a comparative sequence alignment of the amino acid sequences of human, monkey, and mouse TM4SF1 ECL2 domains. The two N-linked glycosylation sites within each ECL2 sequence are underlined, and the epitope on human TM4SF1 recognized by the 8G4 antibody is demarcated. The 8G4 epitope includes the amino acid sequence of human TM4SF1 ECL2 spanning the first and second glycosylation sites (i.e., amino acids 129-161 of human TM4SF1).

FIG. 3A is an image of HUVEC grown on glass discs, immunostained with 8G4, phalloidin, and DAPI without Triton X-100 extraction. 8G4 localized TM4SF1 to the plasma membrane and to cytoplasmic and nuclear sites (white arrows). Scale bar, 10 μm.

FIG. 3B is an enlarged image of Box (i) of FIG. 3A showing that F-actin (phalloidin staining, yellow arrows) extended only into the most proximal portions of nanopodia, the thin, fragile membrane projections from cell surface with roles in cell movement and intercellular interactions.

FIG. 3C is an enlarged image of Box (i) of FIG. 3A showing that 8G4 localized TM4SF1 to nanopodia (pink arrows). The image also shows the phalloidin staining (yellow arrows) of F-actin depicted in FIG. 3B.

FIG. 3D is a series of images of HUVEC grown on glass discs, immunostained with 8G4, phalloidin, and DAPI with Triton X-100 extraction at the specified concentrations. TM4SF1 recognized by 8G4 was largely extracted with 0.05% (but not 0.01%) Triton X-100, though residual perinuclear and nuclear staining (white arrows) required 0.1% Triton X-100 for complete removal. Scale bars, 10 μm.

FIG. 3E are immunoblots stained for TM4SF1 with the 8G4 antibody, showing that all three major (28-, 25-, and 22-kD) TM4SF1 bands were extracted by 0.05% (but not 0.01%) Triton X-100; longer exposure demonstrated residual 28-kD TM4SF1 extraction by 0.1% Triton.

FIG. 3F is an immunoblot stained for TM4SF1 with the 8G4 antibody, showing the subcellular distribution of TM4SF1.

FIG. 4A are immunofluorescence images of human gastric carcinoma-associated vascular endothelial cells (ECs) (pink arrow) immunostained with 8G4, CD144, and DAPI. The human gastric carcinoma-associated vascular ECs demonstrated strong 8G4 staining. The right image is an enlarged image of Box (i) of the left. L, lumen. Scale bars, 10 μm.

FIG. 4B is an immunofluorescence image of normal tissue, adjacent to the gastric carcinoma-associated vascular ECs in FIG. 4A, which demonstrates weak staining of CD144-positive vessels (white arrows). L, lumen. Scale bar, 10 μm.

FIG. 4C is an image of an immuno-nanogold-transmission electron micrograph (TEM) showing 8G4 staining of the EC lining a tumor blood vessel.

FIGS. 4D and 4E are enlarged images of Boxes (i) and (ii) of FIG. 4C showing that intermittent gold particles (pink arrows) decorate the (D) luminal plasma membrane to a much greater extent than the (E) abluminal plasma membrane. Scale bar, 100 nm.

FIG. 4F is an enlarged image of Boxes (iii) of FIG. 4C with blue arrows indicating gold particles in the nucleoplasm. Scale bar, 100 nm.

FIG. 4G is an image of an immuno-nanogold-TEM 8G4 staining of the EC of another tumor vessel, showing the 8G4-labeled nanopodia (green arrows) and stroma-filled, intussusception-like projections that extend into the vascular lumen and form transluminal bridges.

FIG. 4H is an enlarged image of Boxes (i) of FIG. 4G showing the stroma-filled, intussusception-like projections that extend into the vascular lumen and form transluminal bridges. Scale bar, 100 nm.

FIG. 4I is an image of an immuno-nanogold-TEM 8G4 staining of adjacent normal vascular ECs in the stomach.

FIG. 4J is an enlarged image of Box (i) of FIG. 4I showing that the adjacent normal vascular ECs in the stomach lack nanopodia and exhibit much lower luminal (pink arrows) and absent abluminal 8G4 labeling. Scale bar, 100 nm.

FIG. 5A is a series of flow cytometry histograms of trypsinized HUVEC pre-incubated in suspension with 8G4 or control mouse-IgG for 1 h at 4° C., washed 3× with cold PBS, and replated for indicated times (0-24 h), showing that cell surface 8G4 intensity, measured by flow cytometry ($10^4$ cells/measurement), fell from 95.1% to 4.9% over the course of 24 hours.

FIG. 5B is a series of immunocytochemical images showing HUVEC cells replated for 2, 4, or 24 hours and stained with 8G4, phalloidin, and DAPI. The images demonstrate cytoplasmic deposits of 8G4 at 2 hours, increased deposits at 4 hours, and negligible staining at 24 hours.

FIG. 5C is a confocal-3D Z-stack (22 frames; 220 nm/frame from cell surface to matrix) image localizing 8G4 to the nucleoplasm (frame-6, white arrow) of GFP-transduced HUVEC, and also to the perinuclear cytoplasm (frame-15, yellow arrow) at 2 hours.

FIG. 5D is an immunoblot showing both heavy- and light-chains of 8G4 antibody in nuclear extracts that were prepared from 8G4-labeled HUVEC at 0, 4 and 24 h of culture.

FIG. 5E is an immuno-nanogold-TEM image of HUVEC after 2 hours of 8G4 labeling. 8G4 has been endocytosed as demonstrated by the appearance of prominent deposits of 8G4 in the cytoplasm, nuclear pores (red arrows), and nucleoplasm (blue arrow) at 2 h of culture.

FIG. 5F is an enlarged image of Box (i) of FIG. 5E showing that 8G4 is capable of being internalized into TM4SF1-expressing HUVECs.

FIGS. 6A and 6B are confocal-3D Z-stack images (33 frames; 220 nm/frame from cell surface to matrix) of HUVECs cultured on glass discs in 24-well plates following exposure to (A) 200 ng 8G4 and control (Ctl) ADC (saporin-conjugated goat IgG Fab fragment) or (B) 200 ng 8G4 and experimental (Exp) ADC (saporin-conjugated goat anti-mouse Fab fragment) after 4 hours in culture, followed by continued culture for 72 hours with (A) 8G4/Ctl-ADC or (B) 8G4/Exp-ADC before immunocytochemistry, showing high levels of stress fibers in HUVEC exposed to the (ii) 8G4/Exp-ADC compared to (i) 8G4/Ctl-ADC. Individual frames show positive Alexa-594 signal in the nucleus (frame-12 and -16; white arrows) and in the perinuclear cytoplasm (frame-20; yellow arrows).

FIG. 6C is a graph showing >80% killing of HUVEC with 8G4/Exp-ADC compared with Ctl-ADC (p, <0.0001, student t-test) on Day 5 of the MTT assay (see Example 1 below). HUVECs cultured with antibodies alone were unaffected.

Figures 1A, 1B:
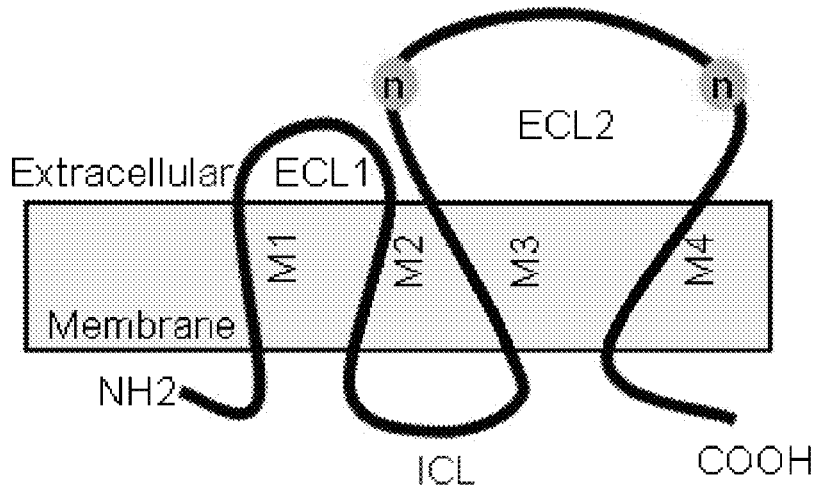
FIG. 1A is an schematic diagram of TM4SF1, showing the two extracellular loops (ECL1 and ECL2) that are separated by four transmembrane domains (M1, M2, M3, and M4), the N- and C-termini, and the intracellular loop (ICL). ECL2 contains two N-glycosylation sites, denoted as "n."
FIG. 1B is a table of the TM4SF1 protein domains and the number of amino acids in each domain.

Other features and advantages of the invention will be apparent from the following Detailed Description and the claims.

DETAILED DESCRIPTION OF EMBODIMENTS OF THE INVENTION

I. Definitions

As used herein, the term "about" means+/−10% of the recited value.

By "transmembrane-4 L six family member-1 (TM4SF1)" "L6," "L6 antigen," "M3S1," "tumor associated antigen L6 (TAAL6)" is meant a polypeptide of the transmembrane 4 superfamily/tetraspanin family, which is highly expressed on tumor vasculature endothelial cells (ECs), tumor cells (TCs), ECs of developing retinal vasculature, and angiogenic blood vessels. TM4SF1 includes, for example, human TM4SF1 protein (NCBI RefSeq No. NP_055035.1), which is 202 amino acids in length.

The terms "antibody" and "immunoglobulin (Ig)" are used interchangeably in the broadest sense and include monoclonal antibodies (e.g., full-length or intact monoclonal antibodies), polyclonal antibodies, multivalent antibodies, multispecific antibodies (e.g., bispecific antibodies so long as they exhibit the desired biological activity) and may also include certain antibody fragments (as described in greater detail herein). An antibody typically comprises both "light chains" and "heavy chains." The light chains of antibodies (immunoglobulins) from any vertebrate species can be assigned to one of two clearly distinct types, called kappa (κ) and lambda (λ), based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively. The subunit structures and three-dimensional configurations of different classes of immunoglobulins are well known.

"Antibody fragments" or "fragments" comprise only a portion of an intact antibody, wherein the portion preferably retains at least one, preferably most or all, of the functions normally associated with that portion when present in an intact antibody. Examples of antibody fragments include Fab, Fab', F(ab')2, and Fv fragments (e.g., single-chain variable fragments (scFv)); diabodies; linear antibodies; single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, ADCC (antibody dependent cell cytotoxicity) function, and complement binding. In one embodiment, an antibody fragment is a monovalent antibody that has an in vivo half life substantially similar to an intact antibody. For example, such an antibody fragment may comprise an antigen binding arm linked to an Fc sequence capable of conferring in vivo stability to the fragment.

As used herein, "variable domain" of an antibody, or fragment thereof, refers to the portions of the light and heavy chains of antibody molecules that include amino acid sequences of complementarity determining regions (CDRs; i.e., CDR-1, CDR-2, and CDR-3), and framework regions (FRs). VH refers to the variable domain of the heavy chain. VL refers to the variable domain of the light chain. According to the methods used in this invention, the amino acid positions assigned to CDRs and FRs may be defined according to Kabat (Sequences of Proteins of Immunological Interest (National Institutes of Health, Bethesda, Md., 1987 and 1991)). Amino acid numbering of antibodies or antigen binding fragments is also according to that of Kabat.

As used herein, the term "complementarity determining regions" or "CDRs" refers to the amino acid residues of an antibody variable domain the presence of which is necessary for antigen binding. Each variable domain typically has three CDR regions identified as CDR-1, CDR-2 and CDR-3. Each complementarity determining region may comprise amino acid residues from a "complementarity determining region" as defined by Kabat (i.e., about residues 24-34 (CDR-L1), 50-56 (CDR-L2) and 89-97 (CDR-L3) in the light chain variable domain and 31-35 (CDR-H1), 50-65 (CDR-H2) and 95-102 (CDR-H3) in the heavy chain variable domain; Kabat et al., *Sequences of Proteins of Immunological Interest,* 5th Ed. Public Health Service, National Institutes of Health, Bethesda, Md. (1991)) and/or those residues from a "hypervariable loop" (i.e., about residues 26-32 (CDR-L1), 50-52 (CDR-L2) and 91-96 (CDR-L3) in the light chain variable domain and 26-32 (CDR-H1), 53-55 (CDR-H2) and 96-101 (CDR-H3) in the heavy chain variable domain; Chothia and Lesk, *J. Mol. Biol.* 196:901-917 (1987)). In some instances, a complementarity determining region can include amino acids from both a CDR region defined according to Kabat and a hypervariable loop.

As used herein, the term "constant domain" of an antibody refers to any domain that is not a variable domain (e.g., CH1, CH2, CH3, and CL domains).

"Framework regions" (hereinafter FR) are those variable domain residues other than the CDR residues. Each variable domain typically has four FRs identified as FR1, FR2, FR3 and FR4. If the CDRs are defined according to Kabat, the light chain FR residues are positioned at about residues 1-23 (LCFR1), 35-49 (LCFR2), 57-88 (LCFR3), and 98-107 (LCFR4) and the heavy chain FR residues are positioned about at residues 1-30 (HCFR1), 36-49 (HCFR2), 66-94 (HCFR3), and 103-113 (HCFR4) in the heavy chain residues. If the CDRs comprise amino acid residues from hypervariable loops, the light chain FR residues are positioned about at residues 1-25 (LCFR1), 33-49 (LCFR2), 53-90 (LCFR3), and 97-107 (LCFR4) in the light chain and the heavy chain FR residues are positioned about at residues 1-25 (HCFR1), 33-52 (HCFR2), 56-95 (HCFR3), and 102-113 (HCFR4) in the heavy chain residues. In some instances, when the CDR comprises amino acids from both a CDR as defined by Kabat and those of a hypervariable loop, the FR residues will be adjusted accordingly. For example, when CDR-H1 includes amino acids H26-H35, the heavy chain FR1 residues are at positions 1-25 and the FR2 residues are at positions 36-49. Common structural features among the variable regions of antibodies, or functional fragments thereof, are well known in the art. The DNA sequence encoding a particular antibody can generally be found following well known methods such as those described in Kabat, et al. 2987 *Sequence of Proteins of Immunological Interest,* U.S. Department of Health and Human Services, Bethesda Md., which is incorporated herein as a reference. In addition, a general method for cloning functional variable regions from antibodies can be found in Chaudhary, V. K., et al., 1990 *Proc. Natl. Acad. Sci. USA* 87:1066, which is incorporated herein as a reference.

The term "monoclonal antibody" as used herein refers to an antibody obtained from a population of substantially homogeneous antibodies, i.e., the individual antibodies comprising the population are identical except for possible mutations, e.g., naturally occurring mutations that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target-binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal-antibody preparation is directed against a single determinant on an antigen. In addition to their specificity, monoclonal-antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein., *Nature* 256:495-497 (1975); Hongo et al., *Hybridoma* 14 (3):253-260 (1995), Harlow et al., *Antibodies: A Laboratory Manual,* (Cold Spring Harbor Laboratory Press, 2nd ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature* 352:624-628 (1991); Marks et al., *J. Mol. Biol.* 222:581-597 (1992); Sidhu et al., *J. Mol. Biol.* 338(2):299-310 (2004); Lee et al., *J. Mol. Biol.* 340(5):1073-1093 (2004); Fellouse, *PNAS USA* 101(34):12467-12472 (2004); and Lee et al., *J. Immunol. Methods* 284(1-2):119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *PNAS USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10:779-783 (1992); Lonberg et al., *Nature* 368:856-859 (1994); Morrison, *Nature* 368:812-813 (1994); Fishwild et al., *Nature Biotechnol.* 14:845-851 (1996); Neuberger, *Nature Biotechnol.* 14:826 (1996); and Lonberg and Huszar, *Intern. Rev. Immunol.* 13:65-93 (1995).

"Chimeric" antibodies (immunoglobulins) have a portion of the heavy and/or light chain identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al. *Nature* 321:522-525 (1986); Riechmann et al. *Nature* 332:323-329 (1988); and Presta. *Curr. Op. Struct. Biol.* 2:593-596 (1992). See also the following review articles and references cited therein: Vaswani and Hamilton. *Ann. Allergy, Asthma & Immunol.* 1:105-115 (1998); Harris. *Biochem. Soc. Transactions* 23:1035-1038 (1995); Hurle and Gross. *Curr. Op. Biotech.* 5:428-433 (1994).

By "binding domain" is meant a part of a compound or a molecule that specifically binds to a target epitope, antigen, ligand, or receptor. Binding domains include but are not limited to antibodies (e.g., monoclonal, polyclonal, recombinant, humanized, and chimeric antibodies), antibody fragments (e.g., fab fragments, fab'2, scfv antibodies, sm ip, domain antibodies, diabodies, minibodies, scfv-fc, sinale domain antibodies, such as AFFIBODIES®, antibody mimetics, such as NANOBODIES®, and domain antibodies), receptors, ligands, aptamers, and other molecules having an identified binding partner.

"Polynucleotide" or "nucleic acid" as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and a basic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. In the present specification, "plasmid" and "vector" may, at times, be used interchangeably as the plasmid is the most commonly used form of vector.

An "epitope" according to this invention refers to amino acid residue(s) of a target polypeptide or antigen that contribute energetically to the binding of an antibody. The binding of the target polypeptide or antigen (e.g., TM4SF1, or a fragment or variant thereof) to the antibody (e.g., an anti-TM4SF1 antibody, e.g., 8G4) can be determined by immunocytochemical analyses. In some embodiments, mutation of any one of the energetically contributing residues of the target polypeptide (for example, mutation of wild-type TM4SF1 by alanine or homolog mutation, or by deletion or truncation) can disrupt the binding of the antibody such that the relative affinity ratio (IC50 mutant TM4SF1/IC50 wild-type TM4SF1) of the antibody may be greater than 1 (e.g., 2, 3, 4, 5, 10, 50, 100, 500, 1000 or greater).

A compound of this invention "which binds" a target polypeptide or antigen of interest is one that binds the target polypeptide or antigen with sufficient affinity such that the compound is useful as a diagnostic and/or therapeutic agent in targeting a cell or tissue expressing the target protein or antigen, and does not significantly cross-react with other proteins. In such embodiments, the extent of binding of the compound to a "non-target" protein will be less than about 10% of the binding of the compound to its particular target protein, as can be determined, for example, by fluorescence activated cell sorting (FACS) analysis, immunohistochemistry, radioimmunoprecipitation (RIA), ELISA, or any other standard quantitative or semi-quantitative technique known in the art.

With regard to the binding of a compound of the invention (e.g., an anti-TM4SF1 antibody) to a target molecule (e.g., a TM4SF1 polypeptide), the terms "specifically binds," "specific binding," and "specific for" with respect to a particular polypeptide target or an epitope on a particular polypeptide target means binding that is measurably different from a non-specific interaction (e.g., a non-specific interaction may be binding to bovine serum albumin or casein). Specific binding can be measured, for example, by determining binding of a molecule compared to binding of a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide target or an epitope on a particular polypeptide target as used herein can be exhibited, for example, by a compound having a Kd for the target of about 1 µM to about 1 fM, alternatively about 200 nM to about 1 fM, alternatively about 200 nM to about 1 pM, alternatively about 150 nM to about 1 fM, alternatively about 150 nM to about 1 pM, alternatively about 100 nM to about 1 fM, alternatively about 100 nM to about 1 pM, alternatively about 60 nM to about 1 fM, alternatively about 60 nM to about 1 pM, alternatively about 50 nM to about 1 fM, alternatively about 50 nM to about 1 pM, alternatively about 30 nM to about 1 fM, alternatively about 30 nM to about 1 pM, alternatively about 20 nM to about 1 fM, alternatively about 20 nM to about 1 pM, alternatively about 10 nM to about 1 fM, alternatively about 10 nM to about 1 pM, alternatively about 8 nM to about 1 fM, alternatively about 8 nM to about 1 pM, alternatively about 6 nM to about 1 fM, alternatively about 6 nM to about 1 pM, alternatively about 4 nM to about 1 fM, alternatively about 4 nM to about 1 pM, alternatively about 2 nM to about 1 fM, alternatively about 2 nM to about 500 pM, alternatively about 1 nM to about 1 fM, alternatively about 1 nM to about 1 pM. In one embodiment, the term "specifically binds" refers to binding where a compound binds to a particular polypeptide target or epitope on a particular polypeptide target without substantially binding to any other polypeptide or polypeptide epitope target.

A "disorder associated with pathological angiogenesis" is any condition that is characterized by new blood vessels growing excessively, insufficiently, or inappropriately (e.g., the location, timing or onset of the angiogenesis being undesired from a medical standpoint) in a diseased state or such that it causes a diseased state, which would benefit from treatment with a compound of the invention or a pharmaceutical composition thereof. Non-limiting examples of disorders to be treated herein include cancers, such as breast cancer, ovarian cancer, renal cancer, colorectal cancer, liver cancer, gastric cancer, and lung cancer; obesity; macular degeneration; diabetic retinopathy; psoriasis; cellular immunity; rheumatoid arthritis; and rosacea.

The terms "cancer" and "cancerous" refer to or describe the physiological condition in mammals that is typically characterized by unregulated cell growth. Included in this definition are benign and malignant cancers as well as dormant tumors or micrometastatses. Examples of cancer include but are not limited to, breast cancer, ovarian cancer, renal cancer, colorectal cancer, liver cancer, gastric cancer, stomach cancer, skin cancer, esophageal cancer, kidney cancer, brain cancer, thyroid cancer, prostate cancer, pancreatic cancer, and lung cancer.

"Tumor," as used herein, refers to all neoplastic cell growth and proliferation, whether malignant or benign, and all pre-cancerous and cancerous cells and tissues. The terms "cancer," "cancerous," "cell proliferative disorder," "proliferative disorder," and "tumor" are not mutually exclusive as referred to herein.

A "chemotherapeutic agent" is a chemical compound useful in the treatment of cancer. Examples of chemotherapeutic agents include, e.g., paclitaxel or topotecan or pegylated liposomal doxorubicin (PLD). Other examples of chemotherapeutic agents include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin; bryostatin; callystatin; CC-1065 (including its adozelesin, carzelesin and bizelesin synthetic analogues);

cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® docetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "growth inhibitory agent" when used herein refers to a compound or composition which inhibits growth and/or proliferation of a cell (e.g., a cell expressing TM4SF1) either in vitro or in vivo. Thus, the growth inhibitory agent may be one which significantly reduces the percentage of TM4SF1-expressing cells. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as the anthracycline antibiotic doxorubicin ((8S-cis)-10-[(3-amino-2,3,6-trideoxy-α-L-lyxo-hexapyranosyl)oxy]-7,8,9,10-tetrahydro-6,8,11-trihydroxy-8-(hydroxyacetyl)-1-methoxy-5,12-naphthacenedione), epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

An "anti-hormonal agent," as used herein, refers to a compound or composition that regulates, reduces, blocks, and/or inhibits the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELI- GARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® GnRH antagonist; lapatinib ditosylate (an ErbB-2 and EGFR dual tyrosine kinase small-molecule inhibitor also known as GW572016); and pharmaceutically acceptable salts, acids or derivatives of any of the above.

The term "linker" as used herein refers to a chemical linking agent (e.g., homobifunctional and heterobifunctional cross-linkers (conjugation agents)) that may include a flexible arm, e.g., 2, 3, 4, 5, 6, 7, 8, 9, 10, 11, 12, 13, 14, or 15 carbon atoms, or one or more amino acids, that covalently link through peptide bonds, one molecule (e.g., a compound of the invention, e.g., an anti-TM4SF1 antibody) to another molecule (e.g., an agent, e.g., a therapeutic agent, e.g., saporin, or a diagnostic agent, e.g., a fluorescent or radioactive label).

The terms "sample" and "biological sample" are used interchangeably to refer to any biological sample obtained from an individual including body fluids, body tissue (e.g., tumor tissue), cells, or other sources. Body fluids are, e.g., lymph, sera, whole fresh blood, peripheral blood mononuclear cells, frozen whole blood, plasma (including fresh or frozen), urine, saliva, semen, synovial fluid and spinal fluid. Samples also include breast tissue, renal tissue, colonic tissue, brain tissue, muscle tissue, synovial tissue, skin, hair follicle, bone marrow, and tumor tissue. Methods for obtaining tissue biopsies and body fluids from mammals are well known in the art.

As used herein, "treatment" (and grammatical variations thereof such as "treat" or "treating") refers to clinical intervention in an attempt to alter the natural course of the individual being treated, and can be performed either for prophylaxis or during the course of clinical pathology and may result in a reduction (e.g., by at least 10%, 15%, 20%, 25%, 30%, 35%, 40%, 45%, 50%, 60%, 70%, 80%, 90%, 95%, 99%, or even 100%) in the progression or severity of a disease or disorder (e.g., disorder associated with pathological angiogenesis, e.g., cancer), or in the progression, severity, or frequency of one or more symptoms of the disease or disorder in a subject (e.g., a human subject). Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis.

By "pharmaceutical composition" is meant a composition containing a compound described herein formulated with a pharmaceutically acceptable carrier, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

A "pharmaceutically acceptable carrier" is meant a carrier which is physiologically acceptable to a treated mammal (e.g., a human) while retaining the therapeutic properties of the compound with which it is administered. One exemplary pharmaceutically acceptable carrier is physiological saline. Other physiologically acceptable carriers and their formulations are known to one skilled in the art and described, for example, in Remington's Pharmaceutical Sciences (18th edition, A. Gennaro, 1990, Mack Publishing Company, Easton, Pa.), incorporated herein by reference.

By "sequence identity" or "sequence similarity" is meant that the identity or similarity between two or more amino acid sequences, or two or more nucleotide sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. These software programs match similar sequences by assigning degrees of homology to various substitutions, deletions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. Additional information can be found at the NCBI web site.

BLASTN is used to compare nucleic acid sequences, while BLASTP is used to compare amino acid sequences. To compare two nucleic acid sequences, the options can be set as follows: -i is set to a file containing the first nucleic acid sequence to be compared (such as C:\seq1.txt); -j is set to a file containing the second nucleic acid sequence to be compared (such as C:\seq2.txt); -p is set to blastn; -o is set to any desired file name (such as C:\output.txt); -q is set to −1; -r is set to 2; and all other options are left at their default setting. For example, the following command can be used to generate an output file containing a comparison between two sequences: C:\Bl2seq-i c:\seq1.txt-j c:\seq2.txt-p blastn-o c:\output.txt-q-1-r 2.

To compare two amino acid sequences, the options of Bl2seq can be set as follows: -i is set to a file containing the first amino acid sequence to be compared (such as C:\seq1.txt); -j is set to a file containing the second amino acid sequence to be compared (such as C:\seq2.txt); -p is set to blastp; -o is set to any desired file name (such as C:\output.txt); and all other options are left at their default setting. For example, the following command can be used to generate an output file containing a comparison between two amino acid sequences: C:\Bl2seq c:\seq1.txt-j c:\seq2.txt-p blastp-o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical amino acid or nucleotide residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. In some examples, for polypeptides, the length of comparison sequences will generally be at least 5, 6, 7, 8, 9, 10, 11, 12, 13, 14, 15, 16, 17, 18, 19, 20, 25, 50, 75, 90, 100, 125, 150, 200, 250, 300, or 350 contiguous amino acids.

The term "therapeutically effective amount" refers to an amount of a compound or composition (e.g., pharmaceutical composition) of the invention to treat a disease or disorder, such as a disorder associated with pathological angiogenesis, in a subject. In the case of a cancer, such as a cancerous tumor, the therapeutically effective amount of the compound or composition may reduce the number of cancer cells; reduce the primary tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the compound or composition may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

By "reduce or inhibit" is meant the ability to cause an overall decrease preferably of 20% or greater, more preferably of 50% or greater, and most preferably of 75%, 85%, 90%, 95%, or greater. Reduce or inhibit can refer to the symptoms of the disorder (e.g., disorder associated with pathological angiogenesis, e.g., cancer) being treated, the presence or size of metastases, the size of the primary tumor, or the size or number of the blood vessels in angiogenic disorders.

As used herein, "administering" is meant a method of giving a dosage of a compound or a composition (e.g., a pharmaceutical composition) to a subject. The compositions utilized in the methods described herein can be administered, for example, intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by inhalation, by injection, by infusion, by continuous infusion, by localized perfusion bathing target cells directly, by catheter, by lavage, in cremes, or in lipid compositions. The preferred method of administration can vary depending on various factors (e.g., the compound or composition being administered and the severity of the condition, disease, or disorder being treated).

Throughout this specification and claims, the word "comprise," or variations such as "comprises" or "comprising," will be understood to imply the inclusion of a stated integer or group of integers but not the exclusion of any other integer or group of integers.

By "subject" is meant a mammal (e.g., a human).

II. Transmembrane-4 L Six Family Member-1 (TM4SF1)

Transmembrane-4 L six family member-1 (TM4SF1) was discovered in 1986 as "L6 antigen" or "tumor cell antigen" (Hellstrom et al. *Cancer Res.* 46: 3917-3923, 1986) because it was abundantly expressed on many cancer cells. Unexpectedly, it was also found to be weakly expressed on the vascular endothelium of blood vessels supplying normal tissues (DeNardo et al. *Int J Rad Appl Instrum B.* 18: 621-631, 1991; Wright et al. *Protein Sci.* 9: 1594-1600, 2000; Richman et al. *Cancer Res.* 5916s-5920s, 1995; O'Donnell et al. *Prostate.* 37: 91-97, 1998).

TM4SF1 is a small plasma membrane glycoprotein (NCBI RefSeq No. NP_055035.1) with tetraspanin topology but not homology (Wright et al. *Protein Sci.* 9: 1594-1600, 2000). It forms TM4SF1-enriched domains (TMED) on plasma membranes, where, like genuine tetraspanins, it serves as a molecular facilitator that recruits functionally related membrane and cytosolic molecules (Shih et al. *Cancer Res.* 69: 3272-3277, 2009; Zukauskas et al., *Angiogenesis.* 14: 345-354, 2011), and plays important roles in cancer cell growth (Hellstrom et al. Cancer Res. 46: 3917-3923, 1986), motility (Chang et al. *Int J Cancer.* 116: 243-252, 2005), and metastasis (Richman et al. *Cancer Res.* 5916s-5920s, 1995).

TM4SF1 is highly expressed by the EC lining the blood vessels supplying several human cancers (Shih et al. *Cancer Res.* 69: 3272-3277, 2009; Zukauskas et al. *Angiogenesis.* 14: 345-354, 2011), by the developing retinal vasculature (English et al. *J Biomed Inform.* 42: 287-295, 2009), and in angiogenic blood vessels induced in mice with an adenovirus expressing VEGF-A (Shih et al. *Cancer Res.* 69: 3272-3277, 2009), though not by many other cell types (Shih et al. *Cancer Res.* 69: 3272-3277, 2009; Zukauskas et al. *Angiogenesis.* 14: 345-354, 2011). Further, TM4SF1 is highly expressed by cultured EC, where it is localized to the plasma membrane and to thin, elongate membrane projections, nanopodia, that extend for up to 50 μm from the cell surface (Shih et al. *Cancer Res.* 69: 3272-3277, 2009; Zukauskas et al. *Angiogenesis.* 14: 345-354, 2011). TM4SF1 regulates EC polarization, proliferation and directed migration (Shih et al. *Cancer Res.* 69: 3272-3277, 2009; Zukauskas et al. *Angiogenesis.* 14: 345-354, 2011).

Taken together, these findings suggested that TM4SF1 had potential as a vascular target for treating cancer. Here, we report evidence favoring this possibility. We prepared a panel of mouse monoclonal antibodies against TM4SF1. We selected one of these antibodies, 8G4, for further study. 8G4 specifically bound to a unique epitope (SEQ ID NO: 1) on extracellular loop-2 (ECL2). Importantly, and surprisingly, upon addition to culture medium, 8G4 was progressively internalized into the EC, and, when complexed with a therapeutic agent (e.g., saporin), caused extensive EC killing. Accordingly, our results strongly suggest that the 8G4 antibody and compounds sharing its unique and novel binding epitope on ECL2 of TM4SF1 can be used for diagnostic and therapeutic therapies, such as methods of treating a subject having a disorder associated with pathological angiogenesis (e.g., cancer).

III. Compounds of the Invention

Accordingly, this invention features compounds including a binding domain which binds (e.g., specifically binds) to a polypeptide at an epitope including an amino acid sequence NYTFASTEGQYLLDTSTWSECTEPKHIVEWNVS (SEQ ID NO: 1). The compounds may include a binding domains that specifically bind to transmembrane-4 L six family member-1 (TM4SF1), or a fragment thereof, such as human TM4SF1 (NCBI RefSeq No. NP_055035.1), or a fragment thereof, at the epitope including SEQ ID NO: 1. In some instances, the human TM4SF1 polypeptide is glycosylated (e.g., N-glycosylated), for example, at residue N129 or residue N159. In some instances, the glycosylated human TM4SF1 polypeptide is glycosylated at both residues N129 and N159. The compound may specifically bind the glycosylated human TM4SF1 with a Kd value that is 10 nM or less (e.g., 10 nM, 5 nM, 2 nM, 1 nM, 500 pM, 100 pM, 50 pM, 1 pM, or 500 fM or less). The compound can include a binding domain including at least one amino acid sequence (e.g., 1, 2, 3, 4, 5, or 6 amino acid sequences) selected from the group consisting of GFTFSSFAMS (SEQ ID NO: 2), TISSGSIYIYYTDGVKG (SEQ ID NO: 3), RGIYYGYDGYAMDY (SEQ ID NO: 4), RSSQSLVHSNGNTYLH (SEQ ID NO: 5), KVSNRFS (SEQ ID NO: 6), and SQSTHIPLA (SEQ ID NO: 7). The compound, for example, may include a binding domain including at least one, at least two, or all three amino acid sequences selected from: GFTFSSFAMS (SEQ ID NO: 2), TISSGSIYIYYTDGVKG (SEQ ID NO: 3), and RGIYYGYDGYAMDY (SEQ ID NO: 4). The compound, for example, may include a binding domain including at least one, at least two, or all three amino acid sequences selected from: RSSQSLVHSNGNTYLH (SEQ ID NO: 5), KVSNRFS (SEQ ID NO: 6), and SQSTHIPLA (SEQ ID NO: 7). The compound, for example, may include a binding domain including the following six amino acid sequences: GFTFSSFAMS (SEQ ID NO: 2), TISSGSIYIYYTDGVKG (SEQ ID NO: 3), RGIYYGYDGYAMDY (SEQ ID NO: 4), RSSQSLVHSNGNTYLH (SEQ ID NO: 5), KVSNRFS (SEQ ID NO: 6), and SQSTHIPLA (SEQ ID NO: 7).

In some embodiments, the compound of the invention can be an antibody, or an antibody fragment thereof. The antibody can be monoclonal, humanized, chimeric, or synthetic. In some instances, the antibody is produced by a hybridoma mouse cell line 8G4-5-13-13F (PTA-120523) (i.e., the 8G4 antibody). In some instances, the heavy chain of the antibody includes an amino acid sequence having at least 60%, 65%, 70%, 75%, or 80% sequence identity (e.g., 81%, 82%, 83%, 84%, 85%, 86%, 87%, 88%, 89%, 90%, 91%, 92%, 93%, 94%, 95%, 96%, 97%, 98%, 99%, or 100/0 identity) to EVILVESGGGLVKPGGSLKLSCAASGFTFSSFAMSWVRQTPEKRLEWVATISSGSIYIYYTDGVKGRFTISRD NAKNTVHLQMSSLRSEDTAMYYCARRGIYYGYDGYAMDYWGQGTSVTVSS (SEQ ID NO: 8). In some instances, the light chain of the antibody includes an amino acid sequence having at least 60%, 65%, 70%, 75%, or 80% sequence identity (e.g., 81%, 82%, 83%, 84%, 85%, 86%, 87%, 88%, 89%, 90%, 91%, 92%, 93%, 94%, 95%, 96%, 97%, 98%, 99%, or 100% identity) to AVVMTQTPLSLPVSLGDQASISCRSSQSLVHSNGNTYLHWYMQKPGQSPKVLIYKVSNRFSGVPDRFSGSG SGTDFTLKISRVEADDLGIYFCSQSTHIPLAFGAGTKLELK (SEQ ID NO: 9). In some instances, the heavy chain of the antibody includes an amino acid sequence having at least 60%, 65%, 70%, 75%, or 80% sequence identity (e.g., 81%, 82%, 83%, 84%, 85%, 86%, 87%, 88%, 89%, 90%, 91%, 92%, 93%, 94%, 95%, 96%, 97%, 98%, 99%, or 100% identity) to EVILVESGGGLVKPGGSLKLSCAASGFTFSSFAMSWVRQTPEKRLEWVATISSGSIYIYYTDGVKGRFTISRD NAKNTVHLQMSSLRSEDTAMYYCARRGIYYGYDGYAMDYWGQGTSVTVSS (SEQ ID NO: 8), and the light chain of the antibody includes an amino acid sequence having at least 60%, 65%, 70%, 75%, or 80% sequence identity (e.g., 81%, 82%, 83%, 84%, 85%, 86%, 87%, 88%, 89%, 90%, 91%, 92%, 93%, 94%, 95%, 96%, 97%, 98%, 99%, or 100% identity) to AVVMTQTPLSLPVSLGDQASISCRSSQSLVHSNGNTYLHWYMQKPGQSPKVLIYKVSNRFSGVPDRFSGSG SGTDFTLKISRVEADDLGIYFCSQSTHIPLAFGAGTKLELK (SEQ ID NO: 9). In some instances, the compound may be a naked, unconjugated, or unmodified compound, such as a naked, unconjugated, or unmodified antibody.

As noted above, the invention features compounds, such as anti-TM4SF1 antibodies, having less than 100% amino acid sequence identity to the amino acid sequences of the heavy and light chain of the 8G4 antibody, described herein. The variant compounds have a lower degree of sequence identity (e.g., less than 100/0 sequence identity, e.g., 90%, 91%, 92%, 93%, 94%, 95%, 96%, 97%, 98%, or 99% sequence identity) but have sufficient similarity so as to perform one or more of the same functions performed by the polypeptides described herein by amino acid sequence. Similarity for a polypeptide is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr and Trp. Guidance concerning which amino acid changes are likely to be phenotypically silent is found in Bowie et al. (*Science.* 247: 1306-1310, 1990) and Table 1 below.

TABLE 1

Conservative Amino Acid Substitutions

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

In some embodiments, a compound of the invention may be a conjugate (i.e., a conjugated compound), which further includes one or more agents (e.g., 1, 2, 3, or 4 or more agents), such as therapeutic agents, that act additively or synergistically with the compound, for example, to kill or inhibit tumor cells (TCs) and/or tumor vasculature endothelial cells (ECs) in the treatment of a disorder associated with pathological angiogenesis, such as cancer. The therapeutic agent, for example, can be a biologically active moiety, such as a cytotoxic agent, a chemotherapeutic agent, a protein, a peptide, an antibody, a growth inhibitory agent, and/or an anti-hormonal agent.

The cytotoxic agent may be, for example, a ribosome inactivating protein (e.g., saporin), a histone deacetylase (HDAC) inhibitor, a tubulin inhibitor, an alkylating agent, an antibiotic, an antineoplastic agent, an antiproliferative agent, an antimetabolite, a topoisomerase I or II inhibitor, a hormonal agonist or antagonist, an immunomodulator, a DNA minor groove binder, and a radioactive agent. Examples of exemplary tubulin inhibitors that can be conjugated, either directly or indirectly, to a compound of the invention include, without limitation, those listed in Table 2 below.

TABLE 2

Exemplary Tubulin Inhibitors

| Classes of Tubulin Inhibitors | Binding Domain | Related Drugs or Analogues |
|---|---|---|
| Polymerization Inhibitors | Vinca Domain | Vinblastine |
| | | Vincristine |
| | | Vinorelbine |
| | | Vinflunine |
| | | Cryptophycin 52 |
| | | Halichondrins |
| | | Dolastatins |
| | | Hemiasterlins |
| | Colchicine Domain | Colchicine |
| | | Combretastatins |
| | | 2-Methoxy-Estradiol |
| | | E7010 |
| Depolymerization Inhibitors | Taxane Site | Paclitaxel (Taxol) |
| | | Docetaxel (Taxotere) |
| | | Epothilon |
| | | Discodermolide |

Chemotherapeutic agents useful for conjugating to compounds of the invention are described. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. See, e.g., WO 93/21232, published Oct. 28, 1993. A variety of radionuclides are available for the production of radioconjugated compounds of the invention. Examples include $^{212}Bi$, $^{131}I$, $^{131}In$, $^{90}Y$, and $^{186}Re$. Alternatively, compounds of the invention may be conjugated to one or more small molecule toxins, such as a calicheamicin, maytansinoids, dolastatins, aurostatins, a trichothecene, and CC1065, and the derivatives of these toxins that have toxin activity, are also contemplated herein. Other therapeutic agents (specifically anticancer agents) that can be conjugated to a compound of the invention include BCNU, streptozoicin, vincristine and 5-fluorouracil, the family of agents known collectively LL-E33288 complex described in U.S. Pat. Nos. 5,053,394 and 5,770,710, as well as esperamicins (U.S. Pat. No. 5,877,296).

For selective destruction of a TC, a compound of the invention may comprise a highly radioactive atom. A variety of radioactive isotopes are available for the production of radioconjugated compounds. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. The radio- or other labels may be incorporated in the conjugate in known ways. For example, the radioconjugated compound of the invention may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al. *Biochem. Biophys. Res. Commun.* 80:49-57, 1978) can be used to incorporate iodine-123. "Monoclonal Antibodies in Immunoscintigraphy" (Chatal, CRC Press 1989) describes other methods in detail.

In some embodiments, a compound of the invention may be a conjugate (i.e., a conjugated compound), which further includes one or more agents (e.g., 1, 2, 3, or 4 or more agents), such as diagnostic agents. The diagnostic agent, for example, can be a label, such as a fluorescent label, a chromogenic label, or a radiolabel. Accordingly, the label may be used for detection purposes, and may be a fluorescent compound, an enzyme, a prosthetic group, a luminescent material, a bioluminescent material, or a radioactive material. The radiolabel, for example, may comprise a radioactive atom for scintigraphic studies, for example $Tc^{99m}$ or $I^{123}$, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

In some embodiments, a compound of the invention may be a conjugate (i.e., a conjugated compound), which includes more than one agent (e.g., 2, 3, or 4 or more agents), wherein at least one agent is a therapeutic agent and at least one agent is a diagnostic agent, such as a therapeutic agent and a diagnostic agent set forth above.

The one or more agents (e.g., therapeutic agents and/or diagnostic agents) may be directly conjugated to a compound of the invention (e.g., by way of a direct covalent or non-covalent interaction), such that the agent is immediately conjugated to the compound. An agent may be directly conjugated to a compound of the invention, for example, by a direct peptide bond. In other instances, the direct conjugation is by way of a direct non-covalent interaction, such as an interaction between a compound of the invention and an agent that specifically binds to the compound (e.g., an antibody agent).

The one or more agents (e.g., therapeutic agents and/or diagnostic agents) may be indirectly conjugated to a compound of the invention (e.g., by way of a linker with direct covalent or non-covalent interactions). Linkers can be chemical linking agents, such as homobifunctional and heterobifunctional cross-linkers, which are available from many commercial sources. Regions available for cross-linking may be found on the compounds (e.g., anti-TM4SF1 antibodies) of the present invention. The linker may comprise a flexible arm, e.g., 2, 3, 4, 5, 6, 7, 8, 9, 10, 11, 12, 13, 14, or 15 carbon atoms. Exemplary linkers include BS3 ([Bis(sulfosuccinimidyl)suberate]; BS3 is a homobifunctional N-hydroxysuccinimide ester that targets accessible primary amines), NHS/EDC (N-hydroxysuccinimide and N-ethyl-(dimethylaminopropyl)carbodimide; NHS/EDC allows for the conjugation of primary amine groups with carboxyl groups), sulfo-EMCS ([N-e-Maleimidocaproic acid]hydrazide; sulfo-EMCS are heterobifunctional reactive groups (maleimide and NHS-ester) that are reactive toward sulfhydryl and amino groups), hydrazide (most proteins contain exposed carbohydrates and hydrazide is a useful reagent for linking carboxyl groups to primary amines), and SATA (N-succinimidyl-S-acetylthioacetate; SATA is reactive towards amines and adds protected sulfhydryls groups).

To form covalent bonds, one can use as a chemically reactive group a wide variety of active carboxyl groups (e.g., esters) where the hydroxyl moiety is physiologically acceptable at the levels required to modify the peptide. Particular agents include N-hydroxysuccinimide (NHS), N-hydroxysulfosuccinimide (sulfo-NHS), maleimide-benzoyl-succinimide (MBS), gamma-maleimido-butyryloxy succinimide ester (GMBS), maleimido propionic acid (MPA) maleimido hexanoic acid (MHA), and maleimido undecanoic acid (MUA).

Primary amines are the principal targets for NHS esters. Accessible α-amino groups present on the N-termini of proteins and the ε-amine of lysine react with NHS esters. An amide bond is formed when the NHS ester conjugation reaction reacts with primary amines releasing N-hydroxysuccinimide. These succinimide containing reactive groups are herein referred to as succinimidyl groups. In certain embodiments of the invention, the functional group on the protein will be a thiol group and the chemically reactive group will be a maleimido-containing group such as gamma-maleimide-butrylamide (GMBA or MPA). Such maleimide containing groups are referred to herein as maleido groups.

The maleimido group is most selective for sulfhydryl groups on peptides when the pH of the reaction mixture is 6.5-7.4. At pH 7.0, the rate of reaction of maleimido groups with sulfhydryls (e.g., thiol groups on proteins such as serum albumin or IgG) is 1000-fold faster than with amines. Thus, a stable thioether linkage between the maleimido group and the sulfhydryl can be formed.

In other embodiments, the linker includes at least one amino acid (e.g., a peptide of at least 2, 3, 4, 5, 6, 7, 10, 15, 20, 25, 40, or 50 amino acids). In certain embodiments, the linker is a single amino acid (e.g., any naturally occurring amino acid such as Cys). In other embodiments, a glycine-rich peptide such as a peptide can be used, as described in U.S. Pat. No. 7,271,149. In other embodiments, a serine-rich peptide linker can be used, as described in U.S. Pat. No. 5,525,491. In some cases, the linker can be a single amino acid (e.g., any amino acid, such as Gly or Cys).

Examples of suitable linkers are succinic acid, Lys, Glu, and Asp, or a dipeptide such as Gly-Lys. When the linker is succinic acid, one carboxyl group thereof may form an amide bond with an amino group of the amino acid residue, and the other carboxyl group thereof may, for example, form an amide bond with an amino group of the peptide or substituent. When the linker is Lys, Glu, or Asp, the carboxyl group thereof may form an amide bond with an amino group of the amino acid residue, and the amino group thereof may, for example, form an amide bond with a carboxyl group of the substituent. When Lys is used as the linker, a further linker may be inserted between the ε-amino group of Lys and the substituent. In one particular embodiment, the further linker is succinic acid which, e.g., forms an amide bond with the ε-amino group of Lys and with an amino group present in the substituent. In one embodiment, the further linker is Glu or Asp (e.g., which forms an amide bond with the ε-amino group of Lys and another amide bond with a carboxyl group present in the substituent), that is, the substituent is a $N^\varepsilon$-acylated lysine residue.

IV. Polynucleotides, Vectors, Host Cells, and Recombinant Methods i. Polynucleotides The invention features polynucleotides encoding one or more (e.g., 1, 2, 3, or 4 or more) of the compounds (e.g., anti-TM4SF1 antibodies, e.g., 8G4) of the invention, or a fragment or portion thereof. Polynucleotide sequences encoding one or more compounds of the invention can be obtained using standard recombinant techniques. For example, cDNA of a compound including a binding domain that specifically binds to a polypeptide at an epitope including the amino acid sequence of SEQ ID NO: 1, or portion thereof, (e.g., 8G4) including one or more (e.g., 1, 2, 3, or 4 or more) cloning sites (e.g., an EcoRV cloning site) can be prepared by polymerase chain reaction (PCR).

ii. Vectors

The invention features vectors including one or more (e.g., 1, 2, 3, or 4 or more) of the compounds of the invention. For example, a polynucleotide of the invention may be isolated and inserted into a replicable vector for further cloning (amplification of the DNA) or for expression of the encoded polypeptide compounds. For example, in instances when the compound is an anti-TM4SF1 antibody, the polynucleotides can be cloned into a pBluescript plasmid and the sequence checked prior to subcloning the DNA into an Fc-encoding plasmid, such as pFUSE-hIgG1-Fc1 (InvivoGen). Many vectors are available. The choice of vector depends in part on the host cell to be used. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al. (U.S. Pat. No. 5,648,237).

In addition, phage vectors containing replicon and control sequences that are compatible with the host microorganism can be used as transforming vectors in connection with these hosts. For example, bacteriophage such as λGEM-11™ may be utilized in making a recombinant vector which can be used to transform susceptible host cells such as *E. coli* LE392.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. An inducible promoter is a promoter that initiates increased levels of transcription of the cistron under its control in response to changes in the culture condition, e.g., the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker to ligate them to cistrons encoding the target light and heavy chains (Siebenlist et al., *Cell.* 20: 269, 1980) using linkers or adaptors to supply any required restriction sites.

iii. Host Cells

The invention features host cells including one or more vectors of the invention, such as host cells of either prokaryotic origin (e.g., *E. coli* cells) or eukaryotic origin (generally mammalian (e.g., human umbilical vein ECs (HUVECs)), but also including fungi (e.g., yeast), insect (e.g., *Drosophila* S2 cells), plant, and nucleated cells from other multicellular organisms). In some embodiments, stable clones can be prepared using a conventional selection method, such as Zeocin selection.

a. Prokaryotic Host Cells

Prokaryotic host cells suitable for expressing compounds (e.g., anti-TM4SF1 antibodies) of the invention include Archaebacteria and Eubacteria, such as Gram-negative or Gram-positive organisms. Examples of useful bacteria include *Escherichia* (e.g., *E. coli*), Bacilli (e.g., *B. subtilis*), Enterobacteria, *Pseudomonas* species (e.g., *P. aeruginosa*), *Salmonella typhimurium*, *Serratia marcescens*, *Klebsiella*, *Proteus*, *Shigella*, *Rhizobia*, *Vitreoscilla*, or *Paracoccus*. In one embodiment, gram-negative cells are used. In one embodiment, *E. coli* cells are used as hosts for the invention. Examples of *E. coli* strains include strain W3110 (Bachmann, Cellular and Molecular Biology, vol. 2 (Washington, D.C.: American Society for Microbiology, 1987), pp. 1190-1219; ATCC Deposit No. 27,325) and derivatives thereof, including strain 33D3 having genotype W3110 ΔfhuA (ΔtonA) ptr3 lac lq lacL8 ΔompTΔ(nmpc-fepE) degP41 kanR (U.S. Pat. No. 5,639,635). Other strains and derivatives thereof, such as *E. coli* 294 (ATCC 31,446), *E. coli* B, *E. coli* λ 1776 (ATCC 31,537) and *E. coli* RV308 (ATCC 31,608) are also suitable. These examples are illustrative rather than limiting. Methods for constructing derivatives of any of the above-mentioned bacteria having defined genotypes are known in the art and described in, for example, Bass et al., Proteins 8:309-314 (1990). It is generally necessary to select the appropriate bacteria taking into consideration replicability of the replicon in the cells of a bacterium. For example, *E. coli*, *Serratia*, or *Salmonella* species can be suitably used as the host when well-known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

b. Eukaryotic Host Cells

The vector components generally include, but are not limited to, one or more of the following: a signal sequence, an origin of replication, one or more marker genes, an enhancer element, a promoter, and a transcription termination sequence.

A vector of the invention for use in a eukaryotic host cell may contain a signal sequence or other polypeptide having a specific cleavage site at the N-terminus of the mature protein or polypeptide of interest. The heterologous signal sequence selected can be one that is recognized and processed (i.e., cleaved by a signal peptidase) by the host cell. In mammalian cell expression, mammalian signal sequences as well as viral secretory leaders, for example, the herpes simplex gD signal, are available. The DNA for such precursor region is ligated in reading frame to DNA encoding the polypeptide.

Generally, an origin of replication component is not needed for mammalian expression vectors. For example, the SV40 origin may typically be used, but only because it contains the early promoter.

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid, and hygromycin.

Another example of suitable selectable markers for mammalian cells are those that enable the identification of cells competent to take up the nucleic acid encoding the compound of the invention (e.g., anti-TM4SF1 antibody, e.g., 8G4), such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding a compound of the invention, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See, for example, U.S. Pat. No. 4,965,199.

Transcription of DNA encoding a compound (e.g., anti-TM4SF1 antibody, e.g., 8G4) by higher eukaryotes can be increased by inserting an enhancer sequence into the vector. Many enhancer sequences are now known from mammalian genes (e.g., globin, elastase, albumin, α-fetoprotein, and insulin genes). Also, one may use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the compound-encoding sequence, provided that enhancement is achieved, but is generally located at a site 5' from the promoter.

Expression and cloning vectors usually contain a promoter that is recognized by the host organism and is operably linked to the nucleic acid sequence(s) encoding the compound (e.g., anti-TM4SF1 antibody, e.g., 8G4). Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly-A tail to the 3' end of the coding sequence. All of these sequences are suitably inserted into eukaryotic expression vectors.

Transcription from vectors encoding the compounds (e.g., anti-TM4SF1 antibodies, e.g., 8G4) in mammalian host cells is controlled, for example, by promoters obtained from the genomes of viruses such as, for example, polyoma virus, fowlpox virus, adenovirus (such as Adenovirus 2), bovine papilloma virus, avian sarcoma virus, cytomegalovirus, a retrovirus, hepatitis-B virus, and Simian Virus 40 (SV40), from heterologous mammalian promoters, e.g., the actin promoter or an immunoglobulin promoter, or from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papillomavirus as a vector is disclosed in U.S. Pat. No. 4,419,446. A modification of this system is described in U.S. Pat. No. 4,601,978. Alternatively, the Rous Sarcoma Virus long terminal repeat can be used as the promoter.

Expression vectors used in eukaryotic host cells will typically also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding a TSP-1 polypeptide. One useful transcription termination component is the bovine growth hormone polyadenylation region (see, e.g., WO 94/11026 and the expression vector disclosed therein).

Suitable host cells for cloning or expressing the DNA in the vectors described herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen. Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)), e.g., CHO-K1 cells; mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

iv. Recombinant Methods

The invention also features methods of producing one or more of the compounds of the invention (e.g., anti-TM4SF1 antibodies, e.g., 8G4) whereby host cells can be cultured in a culture medium, and the compounds of the invention (e.g., anti-TM4SF1 antibodies, e.g., 8G4) can be recovered (e.g., purified) from the host cell or culture medium (e.g., conditioned serum-free media using protein-A Sepharose).

The host cells used to produce a compound of this invention (e.g., anti-TM4SF1 antibody, e.g., 8G4) may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, hydrophobic interaction columns (HIC), ammonium sulfate precipitation, and gel filtration using, for example, Sephadex G-75.

In one embodiment, when the compound is an antibody, Protein A can be immobilized on a solid phase and used for immunoaffinity purification of the antibodies (e.g., 8G4) of the invention. Protein A is a 41-kDa cell wall protein from *Staphylococcus aureus* which binds with a high affinity to the Fc region of antibodies (Lindmark et al. *J. Immunol. Meth.* 62:1-13, 1983). The solid phase to which Protein A is immobilized is preferably a column comprising a glass or silica surface, more preferably a controlled pore glass column or a silicic acid column. In some applications, the column has been coated with a reagent, such as glycerol, in an attempt to prevent nonspecific adherence of contaminants.

As the first step of purification, the preparation derived from the cell culture as described above is applied onto the Protein A immobilized solid phase to allow specific binding of the anti-TM4SF1 antibody of interest to Protein A. The solid phase is then washed to remove contaminants nonspecifically bound to the solid phase. The anti-TM4SF1 antibody of interest may be recovered from the solid phase by elution into a solution containing a chaotropic agent or mild detergent. Exemplary chaotropic agents include, but are not limited to, urea, Guanidine-HCl, lithium perchlorate, Histidine, and Arginine. Exemplary mild detergents include, but are not limited to, Tween (e.g., Tween-20), Triton (e.g., Triton X-100), NP-40 (nonylphenoxylpolyethoxylethanol), Nonidet P-40 (octyl phenoxylpolyethoxylethanol), and Sodium Dodecyl Sulfate (SDS). Diluting the anti-TM4SF1 antibody into a solution containing a chaotropic agent or mild detergent after elution from the column (e.g., mAbSure column) maintains the stability of the anti-TM4SF1 antibody post-elution.

In other embodiments, expressed poly-His tagged compounds of the invention (e.g., anti-TM4SF1 antibodies) can be purified, for example, by $Ni^{2+}$-chelate affinity chromatography as follows. Extracts can be prepared from recombinant virus-infected S2 cells as described by Rupert et al. (*Nature.* 362: 175-179, 1993). Briefly, S2 cells are washed, resuspended in sonication buffer (25 mL HEPES pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate; 300 mM NaCl; 10% glycerol pH 7.8) and filtered through a 0.45 μm filter. A $Ni^{2+}$-NTA agarose column (commercially available from Qiagen) is prepared with a bed volume of 5 mL, washed with 25 mL of water, and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl; 10% glycerol pH 6.0), which elutes nonspecifically bound protein. After reaching $A_{280}$ baseline again, the column is developed with a 0 to 500 mM imidazole gradient in the secondary wash buffer. One mL fractions are collected and analyzed by SDS-PAGE and silver staining or Western blot with $Ni^{2+}$-NTA-conjugated to alkaline phosphatase (Qiagen). Fractions containing the eluted poly-His-tagged compound of the invention are pooled and dialyzed against loading buffer.

Purification of the compound of this invention (e.g., anti-TM4SF1 antibody, e.g., 8G4) can also be performed using known chromatography techniques, including for instance, Protein A or protein G column chromatography. The compound of this invention (e.g., anti-TM4SF1 antibody, e.g., 8G4) may be recovered from the solid phase of the column by elution into a solution containing a chaotropic agent or mild detergent. Exemplary chaotropic agents and mild detergents include, but are not limited to, Guanidine-HCl, urea, lithium perclorate, Arginine, Histidine, SDS (sodium dodecyl sulfate), Tween, Triton, and NP-40, all of which are commercially available. Western blotting (e.g., using a polyclonal antibody to the compound or a conjugated agent, e.g., tag) may be used to confirm that a protein of the correct molecular weight is produced.

V. Compositions of the Invention

Any one of the compounds of the invention (e.g., anti-TM4SF1 antibodies, e.g., 8G4) or polynucleotides encoding the compounds of the invention, such as those described above, can be included in compositions (e.g., pharmaceutical compositions). The pharmaceutical compositions of the invention may further include a pharmaceutically acceptable carrier, excipient, or diluent.

As described herein, any one of the pharmaceutical compositions may be formulated for treating a subject (e.g., a human) having a disorder associated with pathological angiogenesis (e.g., cancer, such as breast cancer, ovarian cancer, renal cancer, colorectal cancer, liver cancer, gastric cancer, and lung cancer; obesity; macular degeneration; diabetic retinopathy; psoriasis; rheumatoid arthritis; cellular immunity; and rosacea).

VI. Methods of Treatment of the Invention

A compound of the invention (e.g., anti-TM4SF1 antibody, e.g., 8G4) that includes a binding domain, which binds (e.g., specifically binds) to a polypeptide at an epitope including an amino acid sequence NYTFASTEGQYLL-DTSTWSECTEPKHIVEWNVS (SEQ ID NO: 1) (e.g., TM4SF1) may be used for therapeutic applications. Accordingly, the invention features methods of treating a subject having a disorder associated with pathological angiogenesis (e.g., cancer, such as breast cancer, ovarian cancer, renal cancer, colorectal cancer, liver cancer, gastric cancer, and lung cancer; obesity; macular degeneration; diabetic retinopathy; psoriasis; rheumatoid arthritis; cellular immunity; and rosacea) including administering a therapeutically effective amount of a compound of the invention or a pharmaceutical composition thereof in order to treat the subject. The compounds or pharmaceutical compositions will be formulated, dosed, and administered in a fashion consistent with good medical practice. Therapy according to the invention may be performed alone or in conjunction with another therapy and may be provided at home, the doctor's office, a clinic, a hospital's outpatient department, or a hospital. Treatment optionally begins at a hospital so that the doctor can observe the therapy's effects closely and make any adjustments that are needed, or it may begin on an outpatient basis. The duration of the therapy depends on the type of disease or disorder being treated, the age and condition of the patient, the stage and type of the patient's disease, and the patient response to the treatment. Additionally, a person having a greater risk of developing a proliferative or pathogenic disease may receive treatment to inhibit or delay the onset of symptoms.

In a method described above, the compound of the invention, or pharmaceutical composition thereof, can be internalized (e.g., endocytosed) into a TM4SF1-expressing cell (e.g., a tumor vasculature endothelial cell or a tumor cell) following binding to the epitope including the amino acid sequence NYTFASTEGQYLLDTSTWSECTEPKHIVEWNVS (SEQ ID NO: 1). In some embodiments, the compound, or pharmaceutical composition thereof, may be internalized into the cytoplasm of the TM4SF1-expressing cell, and may become internalized into the nucleus of the TM4SF1-expressing cell. An therapeutically effective amount of a compound, or pharmaceutical composition thereof, can therefore result in the alleviation, reduction, treatment, and/or cessation of symptoms of the disorder, such as a reduction in primary tumor size (e.g., a reduction, by 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more compared to that of a control treatment, in the size of primary tumors in a subject after administration of the compound or pharmaceutical composition of the invention); a decrease in the number of TM4SF1-expressing cells (e.g., tumor vasculature endothelial cells or tumor cells) (e.g., a decrease, by 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more compared to that of a control treatment, in the number of TM4SF1-expressing cells in a subject after administration of the compound or pharmaceutical composition of the invention); and/or an increase in apoptosis of TM4SF1-expressing cells (e.g., tumor vasculature endothelial cells or tumor cells) (e.g., induction by 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more compared to that of a control treatment in the apoptosis of TM4SF1-expressing cells in the subject after administration of the compound or pharmaceutical composition of the invention). These symptoms and/or other symptoms of a disorder associated with pathological angiogenesis and their resolution during treatment, may be measured by, for example, a physician during a physical examination or by other tests and methods known in the art. In some embodiments, treatment using one or more of the compounds or pharmaceutical compositions of the invention may result in a lack of progression of the disorder in the subject. In other embodiments, treatment using one or more of the compounds, or pharmaceutical compositions thereof, of the invention may result in slowed progression of the disorder in the subject relative to common or conventional therapies (e.g., surgery, radiation therapy, chemotherapy, immunotherapy, or hormonal therapy).

i. Methods of Administration

Compounds and compositions (e.g., pharmaceutical compositions) according to the invention described herein may be formulated to be released immediately upon administration (e.g., targeted delivery) or at any predetermined time period after administration using controlled or extended release formulations. Administration of the compound or composition in controlled or extended release formulations is useful where the compound or composition, either alone or in combination, has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose ($LD_{50}$) to median effective dose ($ED_{50}$)); (ii) a narrow absorption window at the site of release (e.g., the gastro-intestinal tract); or (iii) a short biological half-life, so that frequent dosing during a day is required in order to sustain a therapeutic level.

Many strategies can be pursued to obtain controlled or extended release in which the rate of release outweighs the rate of metabolism of the pharmaceutical composition. For example, controlled release can be obtained by the appropriate selection of formulation parameters and ingredients, including, for example, appropriate controlled release compositions and coatings. Suitable formulations are known to those of skill in the art. Examples include single or multiple unit tablet or capsule compositions, oil solutions, suspensions, emulsions, microcapsules, microspheres, nanoparticles, patches, and liposomes.

Optionally, compositions can be formulated, for example, for administration via a localized drug delivery (e.g., a localized slow- or sustained-release drug delivery system). Suitable examples of sustained-release preparations include semipermeable matrices of solid hydrophobic polymers containing the compound of the invention, which matrices are in the form of shaped articles, e.g., films, or microcapsule. The microcapsules may be prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated, the compounds of the invention (e.g., anti-TM4SF1 antibodies) remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Optionally, the compositions can be formulated, for example, for administration via a viral vector (e.g., an adenovirus vector or a poxvirus vector). Recombinant adenoviruses offer several significant advantages for use as vectors for the expression of, for example, one or more of the compounds of the invention (e.g., anti-TM4SF1 antibodies). The viruses can be prepared to high titer, can infect non-replicating cells, and can confer high-efficiency transduction of target cells ex vivo following contact with a target cell population. Furthermore, adenoviruses do not integrate their DNA into the host genome. Thus, their use as expression vectors has a reduced risk of inducing spontaneous proliferative disorders. In animal models, adenoviral vectors have generally been found to mediate high-level expression for approximately one week. The duration of transgene expression (expression of a nucleic acid molecule of the invention) can be prolonged by using cell or tissue-specific promoters. Other improvements in the molecular engineering of the adenovirus vector itself have produced more sustained transgene expression and less inflammation. This is seen with so-called "second generation" vectors harboring specific mutations in additional early adenoviral genes and "gutless" vectors in which virtually all the viral genes are deleted utilizing a Cre-Lox strategy (Engelhardt et al., *Proc. Natl. Acad. Sci. USA* 91:6196 (1994) and Kochanek et al., *Proc. Natl. Acad. Sci. USA* 93:5731 (1996), each herein incorporated by reference).

Adenoviral vectors disclosed in International Patent Application Publications WO 2006/040330 and WO 2007/104792, each incorporated by reference herein, are particularly useful as vectors of the invention. These adenoviral vectors can encode and/or deliver one or more of the compounds of the invention (e.g., anti-TM4SF1 antibodies) to treat a subject having a pathological condition associated with angiogenesis (e.g., cancer). In some embodiments, one or more recombinant adenovirus vectors can be administered to the subject in order to express more than one type of compound of the invention. Besides adenoviral vectors, other viral vectors and techniques are known in the art that can be used to facilitate delivery and/or expression of one or more of the compounds of the invention in a subject (e.g., a human). These viruses include poxviruses (e.g., vaccinia virus and modified vaccinia virus Ankara (MVA); see, e.g., U.S. Pat. Nos. 4,603,112 and 5,762,938, each incorporated by reference herein), herpesviruses, togaviruses (e.g., Venezuelan Equine Encephalitis virus; see, e.g., U.S. Pat. No. 5,643,576, incorporated by reference herein), picornaviruses (e.g., poliovirus; see, e.g., U.S. Pat. No. 5,639,649, incorporated by reference herein), baculoviruses, and others described by Wattanapitayakul and Bauer (*Biomed. Pharmacother.* 54:487 (2000), incorporated by reference herein).

The compounds and/or compositions utilized in the methods described herein can be formulated, for example, for administration intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularly, mucosally, intrapericardially, intraumbilically, intraocularly, orally, topically, locally, by inhalation, by injection, by infusion, by continuous infusion, by localized perfusion bathing target cells directly, by catheter, by lavage, in cremes, or in lipid compositions.

The preferred method of administration can vary depending on various factors (e.g., the components of the composition being administered and the severity of the condition being treated, e.g., particular stage of cancer). Formulations suitable for oral or nasal administration may consist of liquid solutions, such as an effective amount of the composition dissolved in a diluent (e.g., water, saline, or PEG-400), capsules, sachets, tablets, or gels, each containing a predetermined amount of the composition or polynucleotide encoding the composition of the invention. The pharmaceutical composition may also be an aerosol formulation for inhalation, for example, to the bronchial passageways. Aerosol formulations may be mixed with pressurized, pharmaceutically acceptable propellants (e.g., dichlorodifluoromethane, propane, or nitrogen). In particular, administration by inhalation can be accomplished by using, for example, an aerosol containing sorbitan trioleate or oleic acid, for example, together with trichlorofluoromethane, dichlorofluoromethane, dichlorotetrafluoroethane, or any other biologically compatible propellant gas.

The compositions of the invention may be administered after a subject has been diagnosed with a disorder associated with pathological angiogenesis (e.g., cancer). The composition may be administered to the subject, for example, 15-30 minutes or 1, 2, 3, 4, 5, 6, 7, 8, 9, 10, 12, 20, 24, 48, or 72 hours, 2, 3, 5, or 7 days, 2, 4, 6 or 8 weeks, 3, 4, 6, or 9 months, 1, 2, 3, 4, 5, 6, 7, 8, 9, 10, 15, or 20 years or longer post-diagnosis. The subject can be administered a single dose of the composition(s) (or, e.g., 2, 3, 4, 5, 6, 7, 8, 9, 10, or more doses) or the subject can be administered at least one dose (e.g., 1, 2, 3, 4, 5, 6, 7, 8, 9, 10, or more doses) daily, weekly, monthly, or yearly. The administration period may be defined (e.g., 1-4 weeks, 1-12 months, 1-20 years) or may be for the life of the subject.

When treating a disorder associated with pathological angiogenesis (e.g., cancer), the compositions of the invention may be administered to the subject either before the occurrence of symptoms or a definitive diagnosis or after diagnosis or symptoms become evident. Accordingly, the composition may be administered, for example, immediately after diagnosis or the clinical recognition of symptoms or 2, 4, 6, 10, 15, or 24 hours, 2, 3, 5, or 7 days, 2, 4, 6 or 8 weeks, or even 3, 4, or 6 months after diagnosis or detection of symptoms.

The compositions may be sterilized by conventional sterilization techniques, or may be sterile filtered. The resulting aqueous solutions may be packaged for use as is, or lyophilized, the lyophilized preparation may be administered in powder form or combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of the compound and/or one or more nucleic acids encoding one or more compounds, if desired, such as in a sealed package of tablets or capsules, or in a suitable dry powder inhaler (DPI) capable of administering one or more doses.

ii. Dosages

The dosage administered depends on the subject to be treated (e.g., the age, body weight, capacity of the immune system, and general health of the subject being treated), the form of administration (e.g., as a solid or liquid), the manner of administration (e.g., by injection, inhalation, dry powder propellant), and, potentially, the TM4SF1-expressing cells targeted (e.g., TCs or ECs, such as those of angiogenic vasculature). Additionally, pharmacogenomic (the effect of genotype on the pharmacokinetic, pharmacodynamic, or efficacy profile of a therapeutic) information about a particular patient may affect the dosage used. The composition is preferably administered in an amount that provides a sufficient level of the compound (e.g., anti-TM4SF1 antibody, e.g., 8G4) to yield a therapeutic effect in the subject without undue adverse physiological effects caused by treatment.

The dose of a composition of the invention (e.g., a composition including one or more compounds of the invention) or the number of treatments using a composition of the invention may be increased or decreased based on the severity of, occurrence of, or progression of, the disorder associated with pathological angiogenesis (e.g., cancer) in the subject (e.g., based on the severity of one or more symptoms of the disorder).

A compound or pharmaceutical composition of the invention may be administered to the subject in a dosage of about 0.01 mg/kg to about 10 mg/kg, such as about 0.1 mg/kg to about 10 mg/kg, such as about 3 mg/kg to about 10 mg/kg. In one example, the subject is administered at least one dose (e.g., at least 1, 2, 3, 4, 5, 6, 7, 8, 9, 10, or more doses) of the compound or the pharmaceutical composition. The compound or composition can be administered, for example, between one and seven times a week (e.g., 1, 2, 3, 4, 5, 6, or 7 times a week). Preferably, when a high dose (e.g., about 10 mg/kg) of the compound or the pharmaceutical composition is administered to the subject, a single dose (i.e., one dose) is given in total. Preferably, and when a low dose (e.g., about 3 mg/kg) of the compound or the pharmaceutical composition is administered to the subject, more than one dose (e.g., 2, 3, 4, or 5 or more doses), such as four doses is given in total.

In addition, single or multiple administrations of the compositions of the present invention may be given (pre- or post-diagnosis) to a subject (e.g., one administration or administration two or more times). For example, subjects who are particularly susceptible to, or have a family history of, a disorder associated with pathological angiogenesis, such as cancer, may require multiple treatments to establish and/or maintain a therapeutic effect. For the treatment of a subject having a disorder associated with pathological angiogenesis, the efficacy of treatment provided by the pharmaceutical compositions described herein can be monitored by, for example, monitoring and/or measuring primary tumor size, TM4SF1-expressing cell number, and/or apoptosis of TM4SF1-expressing cells (e.g., tumor vasculature endothelial cells or tumor cells), whereby a reduction or decrease in primary tumor size and/or TM4SF1-expressing cell number and/or an induction or increase in apoptosis of EOC cells in indicative of effective treatment. The dosages may then be adjusted or repeated as necessary to trigger the desired level of response.

A single dose of one or more of the compositions of the invention may achieve a therapeutic effect pre-diagnosis. In addition, a single dose administered post-diagnosis can function as a treatment according to the present invention.

A single dose of one or more of the compositions of the invention can also be used to achieve therapy in subjects being treated for a disease associated with pathological angiogenesis (e.g., cancer). Multiple doses (e.g., 2, 3, 4, 5, or more doses) can also be administered, in necessary, to these subjects.

iii. Carriers, Excipients, Diluents

Therapeutic formulations of the compositions of the invention may be prepared using standard methods known in the art by mixing the active ingredient having the desired degree of purity with optional physiologically acceptable carriers, excipients, or stabilizers (Remington's Pharmaceutical Sciences (20th edition), ed. A. Gennaro, 2000, Lippincott, Williams & Wilkins, Philadelphia, Pa.). Acceptable carriers, include saline, or buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagines, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™, or PEG.

Optionally, but preferably, the formulation contains a pharmaceutically acceptable salt, preferably sodium chloride, and preferably at about physiological concentrations. Optionally, the formulations of the invention can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are preferred preservatives. Optionally, the formulations of the invention can include a pharmaceutically acceptable surfactant at a concentration of 0.005 to 0.02%.

VII. Kits

The invention provides kits that include a composition (e.g., a pharmaceutical composition) of the invention (e.g., a composition including a compound, such as an anti-TM4SF1 antibody, e.g., 8G4, of the invention). The kits include instructions to allow a clinician (e.g., a physician or nurse) to administer the composition contained therein to a subject to treat a disorder associated with pathological angiogenesis (e.g., cancer).

Preferably, the kits include multiple packages of the single-dose pharmaceutical composition(s) containing an effective amount of a polypeptide or polynucleotide of the invention. Optionally, instruments or devices necessary for administering the pharmaceutical composition(s) may be included in the kits. For instance, a kit of this invention may provide one or more pre-filled syringes containing an effective amount of a vaccine, vector, stabilized trimer, or optimized viral polypeptide of the invention. Furthermore, the kits may also include additional components such as instructions regarding administration schedules for a subject having a disorder associated with pathological angiogenesis (e.g., cancer) to use the pharmaceutical composition(s) containing a compound or polynucleotide of the invention.

It will be apparent to those skilled in the art that various modifications and variations can be made in the compositions, methods, and kits of the present invention without departing from the spirit or scope of the invention. Thus, it is intended that the present invention cover the modifications and variations of this invention provided they come within the scope of the appended claims and their equivalents.

EXAMPLES

The following examples are provided to illustrate, but not to limit the presently claimed invention.

Example 1. Materials and Methods

Preparation of Monoclonal Antibodies Against TM4SF1

Human umbilical vein endothelial cells (HUVECs) were cultured in EGM2-MV complete medium (Lonza, Walkersville, Md.) and used at passage 3-6. HUVECs were transduced to overexpress (OE) human TM4SF1 at levels of ~400 mRNA copies/cell (~4× that of native HUVEC) (Shih et al. *Cancer Res.* 69: 3272-3277, 2009; Zukauskas et al. *Angio-*

*genesis*. 14: 345-354, 2011). $10^7$ TM4SF1 OE cells were injected intraperitoneally into female six-week-old Balb-c mice at 2 week intervals ×5. TM4SF1 structure is depicted in FIG. 1. Hybridoma screening steps and epitope mapping strategies are described below and depicted at FIG. 2. Fifteen stable clones were derived. Of these, thirteen recognized epitopes in extracellular loop-2 (ECL2) and two in intracellular domains, based on their reactivity with mutant forms of TM4SF1 (FIGS. 2B-2E). None of the clones directed against human ECL2 reacted with mouse TM4SF1, likely because of significant structural differences between mouse and human TM4SF1 (FIG. 2E).

Immunostaining

Experimental procedures were described previously (Shih et al. *Cancer Res.* 69: 3272-3277, 2009; Zukauskas et al. *Angiogenesis*. 14: 345-354, 2011). Briefly, cells and tissue sections were fixed with 4% paraformaldehyde for 20 min at 25° C., washed in PBS 3×, and blocked with PBS/2% FBS prior to immunocytochemisty with primary antibodies (8G4 or goat anti-human CD144 from Santa Cruz Biotechnology, Santa Cruz, Calif.), followed by secondary donkey anti-mouse Alexa Fluor-488 or -594 labeled antibodies, and Phalloidin (Life Technologies, Carlsbad, Calif.). For immune-nanogold transmission electron microscopy (TEM), goat anti-mouse Alexa Fluor-488/nanogold Fab-fragments (Nanoprobes, Yaphank, N.Y.) were used as secondary antibody. HRP-labeled goat anti-mouse antibodies (Cell Signaling, Danvers, Mass.) were used for immunoblots. Subcellular fractionation kit was acquired from Thermo Scientific (Logan, Utah).

MTT Assays

Saporin-conjugated nonspecific goat Fab (control ADC) and saporin-conjugated goat anti-mouse IgG Fab (experimental ADC) were from Advanced Targeting Systems (San Diego, Calif.), and experiments were performed according to the manufacturer's instructions. Briefly, 200 ng of 8G4 or control mouse IgG (mIgG) were pre-incubated with 200 ng of control- or experimental-ADC in a 10 µl EGM2-MV complete medium (Lonza, Walkersville, Md.) for 1 h at 25° C. The mixture was added to HUVEC plated in 96-well plates ($1 \times 10^3$ cells/well in 200 µl EGM2-MV; 4 wells per group) for 4 h. MTT assays were performed (Life Technologies) on day 5. All experiments were repeated at least 3 times. % viable cells were calculated as follows: Viable Cell (%)=(OD$_{570}$ADC−OD$_{750}$ADC)/(OD$_{570}$Expcontrol−OD$_{750}$Expcontrol)×100.

Example 2. The Anti-TM4SF1 Antibody 8G4

Hybridoma screening and epitope mapping strategies are described in FIG. 2. Of the antibodies directed against an epitope on ECL2 (FIGS. 1A and 1B), 8G4 was selected for detailed study because of its high avidity ($K_d$ ~1 nM).

The 8G4 antibody was deposited by way of its producing hybridoma, hybridoma mouse cell line 8G4-5-13-13F, with the American Type Culture Collection®, PO Box 1549, Manassas, Va., 20108, USA (ATCC®):

| Cell Lines | ATCC® Accession No. | Deposit Date |
|---|---|---|
| Hybridoma mouse Cell line 8G4-5-13-13F | PTA-120523 | Jul. 31, 2013 |

The deposit was made under the provisions of the Budapest Treaty on the International Recognition of the Deposit of Microorganisms for the Purpose of Patent Procedure and the Regulations thereunder (Budapest Treaty). This assures maintenance of a viable deposit for 30 years from the date of deposit. The cell line will be made available by ATCC under the terms of the Budapest Treaty, and subject to an agreement between Beth Israel Deaconess Medical Center, Inc. and ATCC, which assures permanent and unrestricted availability of the cell line to the public upon issuance of the pertinent U.S. patent or upon laying open to the public of any U.S. or foreign patent application, whichever comes first, and assures availability of the cell line to one determined by the U.S. Commissioner of Patents and Trademarks to be entitled thereto according to 35 USC § 122 and the Commissioner's rules pursuant thereto (including 37 CFR § 1.14 with particular reference to 886 OG 638).

The assignee of the present application has agreed that if the deposited cell line should be lost or destroyed when cultivated under suitable conditions, they will be promptly replaced on notification with a specimen of the same cell line. Availability of the deposited cell line is not to be construed as a license to practice the invention in contravention of the rights granted under the authority of any government in accordance with its patent laws.

Example 3. 8G4 and the Subcellular Distribution of TM4SF1 in HUVEC

8G4 stained TM4SF1 in HUVEC (FIGS. 3A-3C) and other cultured endothelial cells (ECs) in intermittent, TM4SF1-enriched domains (TMED) on plasma membrane and nanopodia, and in perinuclear and nuclear deposits. Immunocytochemistry demonstrated that TM4SF1 was extracted by Triton-X100; membrane-associated staining was more greatly affected than that of perinuclear and nuclear deposits (FIG. 3D). TM4SF1 is thought to arise from two transcriptional variants with potential alternative sites for initiation of protein translation, generating isoforms of 28-, 25- and 22-kD (Zukauskas et al. *Angiogenesis*. 14: 345-354, 2011). Immunoblots demonstrated that all three bands were largely extracted by 0.05% but not by 0.01% Triton X-100 (FIG. 3E). Additional extraction with 0.1% Triton eluted residual 28-kD band. The 28-kD band (black arrow) was predominant in the soluble nuclear fraction and present exclusively in cytoskeleton and nuclear chromatin fractions (FIG. 3F). 8G4 did not interact with cells lacking TM4SF1 expression (FIGS. 2C and 2D).

Subcellular fractionation of HUVEC (FIG. 3F) demonstrated all three major TM4SF1 bands in approximately equal amounts in the membrane fraction; all three isoforms were also present in the soluble nuclear fraction. Only the 28-kD TM4SF1 was found in the cytoskeletal and the nuclear chromatin fractions. TM4SF1 was not detected in the soluble cytosolic fraction.

Example 4. Distribution of TM4SF1 in Human Gastric Adenocarcinoma Vascular EC

Previous immunohistochemical studies had demonstrated that TM4SF1 was highly expressed by the EC lining the vasculature of several different human cancers (Chang et al. *Int J Cancer.* 116: 243-252, 2005). Immunofluorescence staining with 8G4 confirmed these results and extended them to an additional human cancer, gastric adenocarcinoma (FIGS. 4A and 4B). Transmission electron microscopy (TEM) with immune-nanogold staining demonstrated intermittent TMED foci on plasma membrane (FIGS. 4C-4F). Luminal staining was consistently stronger than abluminal staining (FIGS. 4D and 4E). Cancer vascular EC also extended thin, lengthy nanopodia with a TMED staining pattern into the vascular lumens for distances of up to 30 µm (FIG. 4G). Some of these extensions were thicker than typical nanopodia, contained collagen stroma, and formed bridges that divided vascular lumens into smaller channels (FIG. 4H). Similar nanopodia-like projections have been described in mouse cancer blood vessels (Nagy et al., Cancer Res. 55: 360-368, 1995) and in blood vessels induced in mice with an adenovirus expressing VEGF-A$^{164}$ (Shih et al., Cancer Res. 69: 3272-3277, 2009). To our knowledge, this is the first description of such projections in human cancer EC and is of significance in that they provide a substantially increased surface area for anti-vascular targeting. Projections of this sort were not found in the EC lining adjacent normal blood vessels, and labeling with 8G4 was also much weaker in such vessels (FIGS. 4I and 4J).

Example 5. 8G4 Internalization in HUVEC

To determine whether 8G4 would be internalized in cells expressing TM4SF1, HUVECs pre-labeled with 8G4 were tracked over time in culture. Flow cytometry revealed progressive loss of cell surface signal: 20.8%, 52.2%, and 95%, at 2, 4, and 24 hours, respectively (FIG. 5A), indicating that 8G4 was progressively endocytosed into HUVECs. While some of this loss could reflect shedding from the cell surface, confocal-3D Z-stack microscopy demonstrated substantial and progressive uptake of 8G4 signal into the cytoplasmic compartment (FIG. 5B) and nucleus (FIG. 5C, frame-6, white arrow). Immunoblots demonstrated both 8G4 heavy- and light-chains in nuclear extracts by 4 hours and these persisted at lower levels at 24 hours (FIG. 5D). Immuno-nanogold-EM provided further evidence for 8G4 endocytosis in that nanogold clusters were identified in the perinuclear cytoplasm, in nuclear pores, and within the nucleus itself (FIGS. 5E and 5F). 8G4 internalization was undetectable in cells that expressed TM4SF1 at very low levels (e.g., fibroblasts).

The pathway(s) responsible for the internalization of the 8G4 antibody remain unclear, but a clathrin-mediated mechanism is unlikely. The kinetics of TMED internalization are slower than those reported for clathrin-dependent endocytosis; 50% loss of TM4SF1 from the HUVEC surface required at least 4 hours (FIGS. 5A and 5B), whereas clathrin-dependent endocytosis typically requires only a few minutes (McNiven. Trends Cell Biol. 16: 487-492, 2006). Also, clathrin inhibitors such as PitStop did not block TM4SF1 uptake, and TM4SF1 intracellular domains do not contain clathrin motifs (Kelly and Owen. Curr Opin Cell Biol. 23: 404-412, 2011). Finally, internalized 8G4 deposits (100-300 nm in diameter) were too large to be accommodated by clathrin-dependent vesicles (~80 nm diameter), and, in any event, they were not membrane-bound. These last observations also exclude 8G4 uptake by caveolae. The entrance of 8G4 into HUVEC nuclei (FIGS. 5A-5F) was unexpected. TM4SF1 does not have classic nuclear localization sequences (Wright et al. Protein Sci. 9: 1594-1600, 2000). It is likely, therefore, that TM4SF1-interacting proteins such as actin and myosin (Shih et al. Cancer Res. 69: 3272-3277, 2009; Zukauskas et al. Angiogenesis. 14: 345-354, 2011) may be responsible (Spencer. Communicative & Integrative Biology. 4: 511-512, 2011; Dzijak et al. PLoS ONE. 7: e30529, 2012; Weber et al. Nature. 431: 325-329, 2004).

Example 6. Targeting TM4SF1 with an Antibody-Drug Conjugate (ADC)

Because 8G4, presumably complexed with TM4SF1, was taken up efficiently by HUVECs, we tested whether an antibody-drug conjugate (ADC) approach would induce EC killing. Recent studies have demonstrated the utility of ADCs as an approach for cancer therapy (Kuroda et al. Prostate. 70: 1286-1294, 2010). Requirements for success are that the target molecule be highly expressed on the cell surface and that the antibody-attached toxin be efficiently endocytosed. TM4SF1 and compounds of the invention, such as the 8G4 anti-TM4SF1 antibody, fulfill these criteria. First, TM4SF1 is expressed highly, not only on the surface of many cancer cells, but also on the plasma membranes of tumor vascular EC, whose killing would be expected to interrupt blood flow and break down the vascular barrier, thereby increasing access of the ADC to tumor cells. Second, the 8G4 antibody directed against TM4SF1 was readily endocytosed by EC and other cells expressing large amounts of TM4SF1, affording cytoplasmic and nuclear access for attached toxins with resultant cell killing. Together, these findings suggest that TM4SF1 may be a suitable vascular and tumor cell target for ADC cancer therapy, such as ADC cancer therapy using compounds of the invention, which specifically bind to an epitope including an amino acid sequence NYTFASTEGQYLLDTSTWSECTEPKH-IVEWNVS (SEQ ID NO: 1) and which are preferably capable of being internalized into the cell in a manner similar or identical to that observed for the 8G4 antibody.

Figure 7:
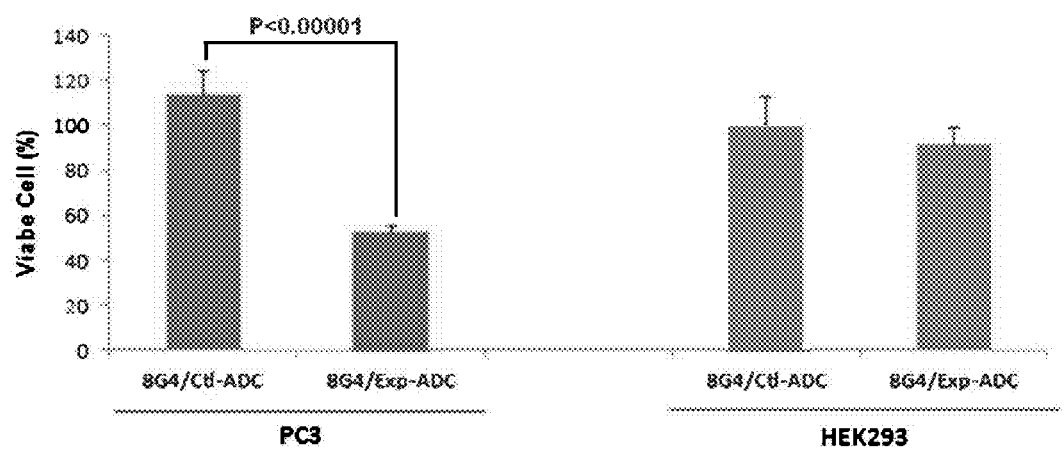
FIG. 7 is a graph showing that 8G4-saporin complex-induced killing is limited to TM4SF1 expressing cells. PC3 tumor cells, which express TM4SF1 at levels similar to HUVEC, or HEK293 cells, which do not express detectable TM4SF1, were cultured in a 96-well ($5 \times 10^3$ cells/well) plate for MTT assays. Cells were cultured with 200 ng 8G4/Ctl-ADC or 8G4/Exp-ADC for 5 days. MTT assay shows >50% killing of PC3 cells (p, <0.00001, Student t-test) in the presence of 8G4 with 8G4/Exp-ADC, but not with 8G4/Ctl-ADC. 8G4/Exp-ADC did not induce detectable cytotoxicity in HEK293 cells.

To test this hypothesis, saporin, a monomeric RNA N-glycosidase that arrests protein synthesis (Polito et al. Int J Biochem Cell Biol. 41: 1055-1061, 2009), was employed as toxin for the generation of an 8G4 ADC. HUVECs ingested 8G4/Exp-ADC (saporin-conjugated goat anti-mouse Fab), developed obvious stress fibers by day-3 (FIG. 6B) and extensive cell killing by day-5 (FIG. 6C). HUVECs that were exposed to 8G4 or mouse-IgG alone, or to control-ADC (saporin-conjugated goat Fab) (FIG. 6A), did not exhibit detectable cytotoxicity (FIG. 6C). Similar results were obtained with PC3 prostate cancer cells that express TM4SF1 at high levels, whereas HEK293, which do not express detectable TM4SF1, were resistant to the 8G4-saporin complex (FIG. 7).

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

All publications, patents, and patent applications are herein incorporated by reference in their entirety to the same extent as if each individual publication, patent, or patent application was specifically and individually indicated to be incorporated by reference in its entirety. Such patent applications specifically include U.S. Provisional Patent Application No. 61/889,340, filed on Oct. 10, 2013, from which this application claims benefit.

What is claimed is:

1. A method of treating tumor angiogenesis in a subject in need thereof comprising administering to said subject a pharmaceutical composition comprising a therapeutically effective amount of an antibody or an antigen-binding fragment thereof, wherein said antibody or antigen-binding fragment thereof comprises a heavy chain variable region comprising the complementarity determining regions (CDRs) of SEQ ID NOs: 2-4, and a light chain variable region comprising first and second CDRs of SEQ ID NOs: 5 and 6, respectively, and a third CDR which is the CDR3 set forth in SEQ ID NO: 9, wherein said antibody or antigen-binding fragment thereof is conjugated to a therapeutic agent, wherein said antibody or antigen-binding fragment thereof binds to a polypeptide sequence in transmembrane-4 L six family member-1 (TM4SF1) that comprises the amino acid sequence of SEQ ID NO: 1 in a glycosylation dependent manner, wherein said polypeptide comprises two glycosylation sites at positions 1 and 30, wherein said positions respectively correspond to residues N129 and N159 of human TM4SF1, and wherein said antibody or antigen-binding fragment thereof treats the tumor angiogenesis.

2. The method of claim 1, wherein said tumor angiogenesis is associated with a cancer.

3. The method of claim 2, wherein said cancer is selected from the group consisting of breast cancer, ovarian cancer, renal cancer, colorectal cancer, liver cancer, stomach cancer, skin cancer, esophageal cancer, kidney cancer, brain cancer, thyroid cancer, prostate cancer, pancreatic cancer, lung cancer, testicular cancer, small bowel cancer, salivary gland cancer, and adrenal cancer.

4. The method of claim 1, wherein said antibody or antigen-binding fragment thereof binds TM4SF1 with a Kd value of 10 nM or less.

5. The method of claim 1, wherein said antibody or antigen-binding fragment thereof binds TM4SF1 with a Kd value of 2 nM or less.

6. The method of claim 1, wherein said antibody or antigen-binding fragment thereof binds TM4SF1 with a Kd value of 500 pM or less.

7. The method of claim 1, wherein said antibody or antigen-binding fragment thereof is internalized into a TM4SF1-expressing cell following binding to said polypeptide.

8. The method of claim 1, wherein said antibody is monoclonal, humanized, chimeric, or synthetic.

9. The method of claim 1, wherein said antibody or antigen-binding fragment thereof is a Fab, Fab', F(ab')$_2$, scFv diabody, or scFv-Fc.

10. The method of claim 1, wherein said therapeutic agent is selected from the group consisting of a cytotoxic agent, a chemotherapeutic agent, a protein, a peptide, an antibody, a growth inhibitory agent, and an anti-hormonal agent.

11. The method of claim 10, wherein said cytotoxic agent is selected from the group consisting of a ribosome inactivating protein, a histone deacetylase (HDAC) inhibitor, a tubulin inhibitor, an alkylating agent, an antibiotic, an antineoplastic agent, an antiproliferative agent, an antimetabolite, a topoisomerase I or II inhibitor, a hormonal agonist or antagonist, an immunomodulator, a DNA minor groove binder, and a radioactive agent.

12. The method of claim 1, wherein the heavy chain variable region of said antibody or antigen-binding fragment thereof comprises the amino acid sequence of SEQ ID NO: 8.

13. The method of claim 1, wherein the heavy chain variable region of said antibody or antigen-binding fragment thereof comprises an amino acid sequence of SEQ ID NO: 9.

14. The method of claim 1, wherein the heavy chain variable region of said antibody or antigen-binding fragment thereof comprises the amino acid sequence of SEQ ID NO: 8 and the light chain variable region of said antibody or antigen-binding fragment thereof comprises the amino acid sequence of SEQ ID NO: 9.

15. The method of claim 1, wherein said antibody or antigen-binding fragment thereof is produced by a hybridoma mouse cell line 8G4-5-13-13F (PTA-120523).

16. A method of treating a tumor angiogenesis in a subject in need thereof comprising administering to said subject a pharmaceutical composition comprising a therapeutically effective amount of an antibody or an antigen-binding fragment thereof conjugated to a therapeutic agent, wherein said antibody or antigen-binding fragment thereof comprises a heavy chain variable region comprising the complementarity determining regions (CDRs) of SEQ ID NOs: 2-4, and a light chain variable region comprising first and second CDRs of SEQ ID NOs: 5 and 6, respectively, and a third CDR which is the CDR3 set forth in SEQ ID NO: 9, wherein said antibody or antigen-binding fragment thereof binds to TM4SF1, and wherein said antibody or antigen-binding fragment thereof treats the tumor angiogenesis.

* * * * *

UNITED STATES PATENT AND TRADEMARK OFFICE
CERTIFICATE OF CORRECTION

PATENT NO. : 10,155,812 B2  
APPLICATION NO. : 15/092486  
DATED : December 18, 2018  
INVENTOR(S) : Shou-Ching S. Jaminet et al.

It is certified that error appears in the above-identified patent and that said Letters Patent is hereby corrected as shown below:

In the Specification

Column 1, Line 31, replace "atheroscleroses" with --atherosclerosis--.

Column 4, Lines 45-46, replace "intravesicularlly" with --intravesicularly--.

Column 6, Line 2, replace "Coraville, Iowa" with --Coralville, Iowa--.

Column 9, Lines 14 and 17, replace "half life" with --half-life--.

Column 12, Line 5, replace "sinale" with --single--.

Column 15, Line 19, replace "chromomycinis" with --chromomycin--.

Column 17, Line 7, replace "formestanie" with --formestane--;  
    Line 19, replace "abherant" with --aberrant--.

Column 20, Lines 13-14, replace "intravesicularlly" with --intravesicularly--.

Column 24, Line 5, replace "sapaonaria" with --saponaria--;  
    Line 18, replace "streptozoicin" with --streptozocin--.

Column 33, Line 14, replace "An" with --A--.

Column 34, Line 34, replace "methylmethacylate" with --methyl methacrylate--.

Column 35, Lines 53-54, replace "intravesicularlly" with --intravesicularly--.

Column 37, Line 54, replace "in necessary" with --if necessary--.

Signed and Sealed this  
Tenth Day of December, 2019

Andrei Iancu  
*Director of the United States Patent and Trademark Office*